US 8,827,661 B2

(12) United States Patent
Mori

(10) Patent No.: US 8,827,661 B2
(45) Date of Patent: Sep. 9, 2014

(54) BLOOD PUMP APPARATUS

(75) Inventor: Takehisa Mori, Tokyo (JP)

(73) Assignee: Thoratec Corporation, Pleasanton, CA (US)

( * ) Notice: Subject to any disclaimer, the term of this patent is extended or adjusted under 35 U.S.C. 154(b) by 357 days.

(21) Appl. No.: 12/975,816

(22) Filed: Dec. 22, 2010

(65) Prior Publication Data

US 2011/0129373 A1 Jun. 2, 2011

Related U.S. Application Data

(63) Continuation of application No. PCT/JP2009/061318, filed on Jun. 22, 2009.

(30) Foreign Application Priority Data

Jun. 23, 2008 (JP) .................................. 2008-163401

(51) Int. Cl.
*F04B 35/04* (2006.01)

(52) U.S. Cl.
USPC .. 417/353; 417/365; 417/423.11; 417/423.14

(58) Field of Classification Search
USPC ................. 417/352, 353, 365, 423.7, 423.11, 417/423.12, 423.14, 424.1, 424.2; 310/87; 600/16
See application file for complete search history.

(56) References Cited

U.S. PATENT DOCUMENTS

| | | | |
|---|---|---|---|
| 1,093,868 A | 4/1914 | Leighty | |
| 2,684,035 A | 7/1954 | Kemp | |
| 3,510,229 A | 5/1970 | Smith | |
| 3,932,069 A | 1/1976 | Giardini et al. | |
| 3,960,468 A | 6/1976 | Boorse et al. | |
| 4,149,535 A | 4/1979 | Volder | |
| 4,382,199 A | 5/1983 | Isaacson | |
| 4,392,836 A | 7/1983 | Sugawara | |
| 4,507,048 A | 3/1985 | Belenger et al. | |
| 4,540,402 A | 9/1985 | Aigner | |
| 4,549,860 A | 10/1985 | Yakich | |

(Continued)

FOREIGN PATENT DOCUMENTS

| | | |
|---|---|---|
| CN | 102239334 A | 11/2011 |
| CN | 102341600 A | 2/2012 |

(Continued)

OTHER PUBLICATIONS

International Search Report (PCT/ISA/210) issued on Jul. 14, 2009, by Japanese Patent Office as the International Searching Authority for International Application No. PCTJP2009/061318.
Asama, et al., "Suspension Performance of a Two-Axis Actively Regulated Consequent-Pole Bearingless Motor," IEEE Transactions on Energy Conversion, vol. 28, No. 4, Dec. 2013, 8 pages.
European Search report Issued in European Patent Application No. 10/748,702.7, mailed Apr. 2, 2013.

(Continued)

*Primary Examiner* — Bryan Lettman
(74) *Attorney, Agent, or Firm* — Kilpatrick Townsend & Stockton LLP

(57) ABSTRACT

A blood pump apparatus includes a housing having a blood inlet port and blood outlet port, a pump unit including an impeller that rotates within the housing, and an impeller rotational torque generation section. The housing includes a plurality of magnetic members embedded between the impeller and the impeller rotational torque generation section for transmitting a magnetically attractive force generated by the impeller rotational torque generation section to an impeller body. The pump device includes a non-contact bearing mechanism for rotating the impeller without contacting with the inner surface of the housing when the impeller is rotated by the impeller rotational torque generation section.

26 Claims, 13 Drawing Sheets

(56) References Cited

U.S. PATENT DOCUMENTS

| | | |
|---|---|---|
| 4,686,982 A | 8/1987 | Nash |
| 4,688,998 A | 8/1987 | Olsen et al. |
| 4,753,221 A | 6/1988 | Kensey et al. |
| 4,769,006 A | 9/1988 | Papantonakos |
| 4,790,843 A | 12/1988 | Carpentier et al. |
| 4,806,080 A | 2/1989 | Mizobuchi et al. |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,930,997 A | 6/1990 | Bennett |
| 4,944,722 A | 7/1990 | Carriker et al. |
| 4,957,504 A | 9/1990 | Chardack |
| 4,969,865 A | 11/1990 | Hwang et al. |
| 4,985,014 A | 1/1991 | Orejola |
| 4,995,857 A | 2/1991 | Arnold |
| 5,092,844 A | 3/1992 | Schwartz et al. |
| 5,092,879 A | 3/1992 | Jarvik |
| 5,106,263 A | 4/1992 | Irie |
| 5,106,273 A | 4/1992 | Lemarquand et al. |
| 5,106,372 A | 4/1992 | Ranford |
| 5,112,202 A | 5/1992 | Oshima et al. |
| 5,112,349 A | 5/1992 | Summers et al. |
| 5,129,883 A | 7/1992 | Black |
| 5,145,333 A | 9/1992 | Smith |
| 5,147,186 A | 9/1992 | Buckholtz |
| 5,190,528 A | 3/1993 | Fonger et al. |
| 5,201,679 A | 4/1993 | Velte et al. |
| 5,211,546 A | 5/1993 | Isaacson et al. |
| 5,275,580 A | 1/1994 | Yamazaki |
| 5,290,227 A | 3/1994 | Pasque |
| 5,290,236 A | 3/1994 | Mathewson |
| 5,306,295 A | 4/1994 | Kolff et al. |
| 5,312,341 A | 5/1994 | Turi |
| 5,332,374 A | 7/1994 | Kricker et al. |
| 5,346,458 A | 9/1994 | Affeld |
| 5,354,331 A | 10/1994 | Schachar |
| 5,360,445 A | 11/1994 | Goldowsky |
| 5,370,509 A | 12/1994 | Golding et al. |
| 5,385,581 A | 1/1995 | Bramm et al. |
| 5,405,383 A | 4/1995 | Barr |
| 5,449,342 A | 9/1995 | Hirose et al. |
| 5,478,222 A * | 12/1995 | Heidelberg et al. ............ 417/414 |
| 5,504,978 A | 4/1996 | Meyer, III |
| 5,507,629 A | 4/1996 | Jarvik |
| 5,533,957 A | 7/1996 | Aldea |
| 5,569,111 A | 10/1996 | Cho et al. |
| 5,575,630 A | 11/1996 | Nakazawa et al. |
| 5,595,762 A | 1/1997 | Derrieu et al. |
| 5,611,679 A | 3/1997 | Ghosh et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman, Jr. et al. |
| 5,695,471 A | 12/1997 | Wampler |
| 5,725,357 A | 3/1998 | Nakazeki et al. |
| 5,738,649 A | 4/1998 | Macoviak |
| 5,746,575 A | 5/1998 | Westphal et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,800,559 A | 9/1998 | Higham et al. |
| 5,807,311 A | 9/1998 | Palestrant |
| 5,814,011 A | 9/1998 | Corace |
| 5,824,069 A | 10/1998 | Lemole |
| 5,851,174 A | 12/1998 | Jarvik et al. |
| 5,853,394 A | 12/1998 | Tolkoff et al. |
| 5,868,702 A | 2/1999 | Stevens et al. |
| 5,868,703 A | 2/1999 | Bertolero et al. |
| 5,890,883 A | 4/1999 | Golding et al. |
| 5,924,848 A | 7/1999 | Izraelev |
| 5,924,975 A | 7/1999 | Goldowsky |
| 5,928,131 A | 7/1999 | Prem |
| 5,938,412 A | 8/1999 | Izraelev |
| 5,941,813 A | 8/1999 | Sievers et al. |
| 5,947,703 A | 9/1999 | Nojiri et al. |
| 5,951,263 A | 9/1999 | Taylor et al. |
| 5,964,694 A | 10/1999 | Siess et al. |
| 6,004,269 A | 12/1999 | Crowley et al. |
| 6,007,479 A | 12/1999 | Rottenberg et al. |
| 6,030,188 A | 2/2000 | Nojiri et al. |
| 6,042,347 A | 3/2000 | Scholl et al. |
| 6,053,705 A | 4/2000 | Schob et al. |
| 6,058,593 A | 5/2000 | Siess |
| 6,066,086 A | 5/2000 | Antaki et al. |
| 6,071,093 A | 6/2000 | Hart |
| 6,074,180 A | 6/2000 | Khanwilkar et al. |
| 6,080,133 A | 6/2000 | Wampler |
| 6,086,527 A | 7/2000 | Talpade |
| 6,100,618 A | 8/2000 | Schoeb et al. |
| 6,123,659 A | 9/2000 | leBlanc et al. |
| 6,123,726 A | 9/2000 | Mori et al. |
| 6,139,487 A | 10/2000 | Siess |
| 6,142,752 A | 11/2000 | Akamatsu et al. |
| 6,143,025 A | 11/2000 | Stobie et al. |
| 6,146,325 A | 11/2000 | Lewis et al. |
| 6,149,683 A | 11/2000 | Lancisi et al. |
| 6,158,984 A | 12/2000 | Cao et al. |
| 6,171,078 B1 | 1/2001 | Schob |
| 6,176,822 B1 | 1/2001 | Nix et al. |
| 6,176,848 B1 | 1/2001 | Rau et al. |
| 6,190,304 B1 | 2/2001 | Downey et al. |
| 6,206,659 B1 | 3/2001 | Izraelev |
| 6,227,797 B1 | 5/2001 | Watterson et al. |
| 6,227,820 B1 | 5/2001 | Jarvik |
| 6,234,772 B1 | 5/2001 | Wampler et al. |
| 6,234,998 B1 | 5/2001 | Wampler |
| 6,245,007 B1 | 6/2001 | Bedingham et al. |
| 6,247,892 B1 | 6/2001 | Kazatchkov et al. |
| 6,254,359 B1 | 7/2001 | Aber |
| 6,264,635 B1 | 7/2001 | Wampler et al. |
| 6,293,901 B1 | 9/2001 | Prem |
| 6,295,877 B1 | 10/2001 | Aboul-Hosn et al. |
| 6,319,231 B1 | 11/2001 | Andrulitis |
| 6,351,048 B1 | 2/2002 | Schob et al. |
| 6,375,607 B1 | 4/2002 | Prem |
| 6,422,990 B1 | 7/2002 | Prem |
| 6,425,007 B1 | 7/2002 | Messinger |
| 6,428,464 B1 | 8/2002 | Bolling |
| 6,439,845 B1 | 8/2002 | Veres |
| 6,447,266 B2 | 9/2002 | Antaki et al. |
| 6,447,441 B1 | 9/2002 | Yu et al. |
| 6,458,163 B1 | 10/2002 | Slemker et al. |
| 6,508,777 B1 | 1/2003 | Macoviak et al. |
| 6,508,787 B2 | 1/2003 | Widmann et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | deBlanc et al. |
| 6,547,530 B2 * | 4/2003 | Ozaki et al. ................. 417/44.1 |
| 6,595,762 B2 | 7/2003 | Khanwilkar et al. |
| 6,609,883 B2 | 8/2003 | Woodard et al. |
| 6,623,420 B2 | 9/2003 | Reich et al. |
| 6,641,558 B1 | 11/2003 | Aboul-Hosn et al. |
| 6,688,861 B2 | 2/2004 | Wampler |
| 6,692,318 B2 | 2/2004 | McBride |
| 6,698,097 B1 | 3/2004 | Miura et al. |
| 6,709,418 B1 | 3/2004 | Aboul-Hosn et al. |
| 6,716,189 B1 | 4/2004 | Jarvik et al. |
| 6,776,578 B2 | 8/2004 | Belady |
| 6,790,171 B1 | 9/2004 | Grinderman et al. |
| 6,794,789 B2 | 9/2004 | Siess et al. |
| 6,808,371 B2 | 10/2004 | Niwatsukino et al. |
| 6,817,836 B2 | 11/2004 | Nose et al. |
| 6,860,713 B2 | 3/2005 | Hoover |
| 6,926,662 B1 | 8/2005 | Aboul-Hosn et al. |
| 6,935,344 B1 | 8/2005 | Aboul-Hosn et al. |
| 6,942,672 B2 | 9/2005 | Heilman et al. |
| 6,949,066 B2 | 9/2005 | Bearnson et al. |

(56) References Cited

U.S. PATENT DOCUMENTS

| | | |
|---|---|---|
| 6,974,436 B1 | 12/2005 | Aboul-Hosn et al. |
| 6,991,595 B2 | 1/2006 | Burke et al. |
| 7,010,954 B2 | 3/2006 | Siess et al. |
| 7,011,620 B1 | 3/2006 | Siess |
| 7,027,875 B2 | 4/2006 | Siess et al. |
| 7,048,681 B2 | 5/2006 | Tsubouchi et al. |
| 7,112,903 B1 | 9/2006 | Schob |
| 7,128,538 B2 | 10/2006 | Tsubouchi et al. |
| 7,156,802 B2 | 1/2007 | Woodard et al. |
| 7,160,243 B2 | 1/2007 | Medvedev |
| 7,172,551 B2 | 2/2007 | Leasure |
| 7,175,588 B2 | 2/2007 | Morello |
| 7,241,257 B1 | 7/2007 | Ainsworth et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,431,688 B2 | 10/2008 | Wampler et al. |
| 7,467,930 B2 | 12/2008 | Ozaki et al. |
| 7,470,246 B2 | 12/2008 | Mori et al. |
| 7,491,163 B2 | 2/2009 | Viole et al. |
| 7,575,423 B2 | 8/2009 | Wampler |
| 7,645,225 B2 | 1/2010 | Medvedev et al. |
| 7,699,586 B2 | 4/2010 | LaRose et al. |
| 7,731,675 B2 | 6/2010 | Aboul-Hosn et al. |
| 7,748,964 B2 | 7/2010 | Yaegashi et al. |
| 7,802,966 B2 | 9/2010 | Wampler et al. |
| 7,841,976 B2 | 11/2010 | McBride et al. |
| 7,888,242 B2 | 2/2011 | Tanaka et al. |
| 7,934,909 B2 | 5/2011 | Nuesser et al. |
| 7,976,271 B2 | 7/2011 | Larose et al. |
| 7,997,854 B2 | 8/2011 | Larose et al. |
| 8,007,254 B2 | 8/2011 | Larose et al. |
| 8,096,935 B2 | 1/2012 | Sutton et al. |
| 8,123,669 B2 | 2/2012 | Siess et al. |
| 8,226,373 B2 | 7/2012 | Yaegashi |
| 8,282,359 B2 | 10/2012 | Ayre et al. |
| 8,283,829 B2 | 10/2012 | Yamamoto et al. |
| 8,366,381 B2 | 2/2013 | Woodard et al. |
| 8,403,823 B2 | 3/2013 | Yu et al. |
| 8,512,012 B2 | 8/2013 | Akdis et al. |
| 2002/0058994 A1 | 5/2002 | Hill et al. |
| 2002/0095210 A1 | 7/2002 | Finnegan et al. |
| 2003/0023302 A1 | 1/2003 | Moe et al. |
| 2004/0007515 A1 | 1/2004 | Geyer |
| 2004/0024285 A1 | 2/2004 | Muckter |
| 2004/0030381 A1 | 2/2004 | Shu |
| 2004/0210305 A1 | 10/2004 | Shu et al. |
| 2005/0089422 A1 | 4/2005 | Ozaki et al. |
| 2005/0287022 A1 | 12/2005 | Yaegashi et al. |
| 2006/0024182 A1 | 2/2006 | Akdis et al. |
| 2006/0055274 A1 | 3/2006 | Kim |
| 2007/0078293 A1 | 4/2007 | Shambaugh et al. |
| 2007/0134993 A1 | 6/2007 | Tamez et al. |
| 2007/0213690 A1 | 9/2007 | Phillips et al. |
| 2007/0231135 A1 | 10/2007 | Wampler et al. |
| 2007/0297923 A1 | 12/2007 | Tada |
| 2008/0021394 A1* | 1/2008 | LaRose et al. ............ 604/151 |
| 2008/0030895 A1 | 2/2008 | Obara et al. |
| 2008/0124231 A1* | 5/2008 | Yaegashi ............... 417/417 |
| 2009/0060743 A1 | 3/2009 | McBride et al. |
| 2009/0074336 A1 | 3/2009 | Engesser et al. |
| 2009/0171136 A1 | 7/2009 | Shambaugh, Jr. |
| 2011/0118766 A1 | 5/2011 | Reichenbach et al. |
| 2011/0118829 A1 | 5/2011 | Hoarau et al. |
| 2011/0243759 A1 | 10/2011 | Ozaki et al. |
| 2011/0318203 A1 | 12/2011 | Ozaki et al. |
| 2012/0003108 A1 | 1/2012 | Ozaki et al. |
| 2012/0016178 A1 | 1/2012 | Woodard et al. |
| 2012/0035411 A1 | 2/2012 | Larose et al. |
| 2012/0078030 A1 | 3/2012 | Bourque |
| 2012/0130152 A1 | 5/2012 | Ozaki et al. |
| 2012/0243759 A1 | 9/2012 | Fujisawa |
| 2012/0308363 A1 | 12/2012 | Ozaki et al. |
| 2013/0121821 A1 | 5/2013 | Ozaki et al. |
| 2013/0170970 A1 | 7/2013 | Ozaki et al. |
| 2013/0178694 A1 | 7/2013 | Jeffery et al. |
| 2013/0243623 A1 | 9/2013 | Okawa et al. |
| 2014/0030122 A1 | 1/2014 | Ozaki et al. |

FOREIGN PATENT DOCUMENTS

| | | |
|---|---|---|
| EP | 1113117 A2 | 7/2001 |
| EP | 1495773 A2 | 1/2005 |
| EP | 1495773 A3 | 11/2006 |
| EP | 1495773 B1 | 2/2009 |
| EP | 2372160 A1 | 10/2011 |
| EP | 2405140 A1 | 1/2012 |
| EP | 2461465 A1 | 6/2012 |
| JP | 04/091396 A | 3/1992 |
| JP | 04/148094 A | 5/1992 |
| JP | 05/021197 U | 5/1992 |
| JP | 06/014538 U | 2/1994 |
| JP | 06/053790 U | 7/1994 |
| JP | 07/014220 U | 3/1995 |
| JP | 7-42869 U | 8/1995 |
| JP | 07/509156 A | 10/1995 |
| JP | 9-122228 A | 5/1997 |
| JP | 10/331841 A | 12/1998 |
| JP | 11-244377 A | 9/1999 |
| JP | 2001/309628 | 11/2001 |
| JP | 2003-135592 A | 5/2003 |
| JP | 2004/166401 A | 6/2004 |
| JP | 2004/209240 A | 7/2004 |
| JP | 2004-332566 A | 11/2004 |
| JP | 20048/346925 A | 12/2004 |
| JP | 2005/127222 A | 5/2005 |
| JP | 2005/270345 A | 10/2005 |
| JP | 2005/270415 A | 10/2005 |
| JP | 2005/287599 A | 10/2005 |
| JP | 2006/167173 A | 6/2006 |
| JP | 2007/002885 A | 1/2007 |
| JP | 2007/043821 | 2/2007 |
| JP | 2007-089972 A | 4/2007 |
| JP | 2007/089974 | 4/2007 |
| JP | 2007/215292 | 8/2007 |
| JP | 2007/247489 | 9/2007 |
| JP | 2008/104278 | 5/2008 |
| JP | 2008-132131 A | 6/2008 |
| JP | 2008/297997 A | 12/2008 |
| JP | 2010/136863 A | 6/2010 |
| WO | 93/07388 A1 | 4/1993 |
| WO | 96/31934 | 10/1996 |
| WO | 97/42413 A1 | 11/1997 |
| WO | 2005/028000 A1 | 3/2005 |
| WO | 2005/034312 A2 | 4/2005 |
| WO | 2010/067682 A1 | 6/2010 |
| WO | 2010/101082 A1 | 9/2010 |
| WO | 2011/013483 A1 | 2/2011 |

OTHER PUBLICATIONS

Extended European Search Report issued in European Patent Application No. EP 10748677.1, mailed Nov 19, 2012.
International Search Report and Written Opinion issued in PCT/JP2011/050925, mailed Apr. 12,2011.
International Search Report and Written Opinion issued in PCT/JP2011/054134, mailed Apr. 12,2011.
International Search Report and Written Opinion issued in PCT/JP2011/064768, mailed Sep. 13, 2011.
International Search Report and Written Opinion issued in PCT/JP2011/070450, mailed Dec. 13, 2011.
Kosaka, et al.,"Operating Point Control System for a Continuous Flow Artificial Heart: In Vitro Study," ASAIO Journal 2003, 6 pages.
Supplementary European Search Report issued in European Application No. 09/831,788.6, dated Jan. 7, 2013, 7 pages.
Terumo Heart, Inc., "Handled With Care—Significantly Reduce the Risk of Cell Damage," Terumo brochure, Apr. 2010, 2 pages.
Yamazaki, et al., "Development of a Miniature Intraventricular Axial Flow Blood Pump," ASAIO Journal, 1993, 7 pages.

* cited by examiner

BLOOD PUMP APPARATUS

This application is a continuation of International Application No. PCT/JP2009/061318 filed on Jun. 22, 2009 and claims priority to Japanese Application No. 2008-163401 filed on Jun. 23, 2008, the entire content of both of which is incorporated herein by reference.

TECHNOLOGICAL FIELD

The present invention generally pertains to blood pumps, more specifically a blood pump apparatus for feeding blood.

BACKGROUND DISCUSSION

Recently, there have been an increasing number of instances in which a centrifugal blood pump is used as a heart assisting pump for assisting a heart or for extracorporeal blood circulation in a pump-oxygenator. Proposals have been made of a centrifugal blood pump of the type embedded in a living body.

One example of a centrifugal pump involves a system in which a driving torque from an external motor is transmitted by use of magnetic coupling, in view of the fact that physical communication between the exterior and a blood chamber in the pump is totally precluded so that penetration of bacteria and the like can be prevented. Such a centrifugal blood pump includes a housing having a blood inlet port and a blood outlet port, and an impeller which rotates within the housing and which feeds blood by a centrifugal force during rotation. In addition, the impeller is provided with a permanent magnet, and is rotated by a rotation torque generating mechanism which includes a rotor having a magnet for attracting the magnet of the impeller and a motor for rotating the rotor. The impeller is attracted also toward the opposite side to the rotor, and is rotated without contacting with the housing.

In the centrifugal blood pump apparatus of the intracorporeally embedded type described Japanese Patent Laid-open No. 2003-135592, a metallic material is used for making the housing for the purpose of using the apparatus for a long time. On the other hand, the blood pump apparatus described in Japanese Patent Laid-open No. Hei 09-122228 and the blood pump apparatus described in Japanese Patent Laid-open No. Hei 11-244377 use a plastic material to form the housing. The housing in this case is required to have a certain extent of thickness for securing strength of the main body of the pump apparatus, and this structure leads to a concern that the rotating magnetic force applied to the impeller by the impeller rotational torque generation section might be lowered.

SUMMARY

The inventor here has discovered that where a magnetic material is provided in the housing on the impeller rotational torque generation section side, the impeller rotating torque generating unit is enabled to attract the impeller and rotate the impeller, without increasing the magnetic force or size of the impeller magnetic material and while providing sufficient thickness of the housing.

According to one aspect, a blood pump apparatus comprises a housing having a blood inlet port and a blood outlet port, a pump unit including an impeller rotatably mounted within the housing and provided with a plurality of magnetic material bodies, the impeller being rotatable within the housing to feed blood, and the magnetic material members rotating together with the impeller, an impeller rotational torque generation section for generating a magnetically attractive force to rotate the impeller, a plurality of magnetic members embedded in the housing between the impeller and the impeller rotational torque generation section for transmitting the magnetically attractive force generated by the impeller rotational torque generation section to the magnetic material members of the impeller, and a non-contact bearing mechanism for rotating the impeller without the impeller contacting an inner surface of the housing when the impeller is rotated by the impeller rotational torque generation section.

According to another aspect, a blood pump apparatus comprises a housing including a blood inlet port through which blood enters the housing and a blood outlet port through which blood exits the housing, a hollow interior in the housing defining a blood chamber in fluid communication with the blood inlet and the blood outlet, an impeller rotatably positioned in the blood chamber to feed blood, a plurality of magnetic material members mounted on the impeller so that the impeller and the plurality of magnetic material members rotate together as a unit within the blood chamber in the housing, a motor stator positioned adjacent the housing for generating a magnetically attractive force to rotate the impeller, and a plurality of spaced apart magnetic members each positioned in a respective recess in the housing situated between the impeller and the motor stator so that the magnetic members transmit the magnetically attractive force generated by the motor stator to the magnetic material members of the impeller. A non-contact bearing mechanism rotates the impeller without the impeller contacting the inner surface of the housing when the impeller is rotated by the motor stator.

A blood pump apparatus according to another aspect includes a housing having a blood inlet port through which blood enters the housing and a blood outlet port through which blood exits the housing, wherein the housing comprises a first housing member and a second housing member configured so that a blood chamber is formed between the first and second housing members, with the blood chamber fluidly communicating with the blood inlet and the blood outlet. An impeller is rotatably positioned in the blood chamber to feed blood, and a plurality of first magnetic material members are integrated with the impeller so that the impeller and the plurality of magnetic material members rotate together as a unit within the blood chamber in the housing. The impeller possesses oppositely facing surfaces each of which faces a respective inner surface of the housing. A motor stator is positioned adjacent the housing to generate a magnetically attractive force to rotate the impeller. A plurality of spaced apart magnetic members each positioned in a respective recess in the second housing member so that the magnetic members are located between the impeller and the impeller rotational torque generation section for transmitting the magnetically attractive force generated by the impeller rotational torque generation section to the magnetic material members of the impeller. A non-contact bearing mechanism rotates the impeller without the impeller contacting the inner surface of the housing when the impeller is rotated by the motor stator. The non-contact bearing mechanism comprises at least one of: i) a plurality of spaced apart grooves provided on at least one of said oppositely facing surfaces of the impeller or at least one of said inner surfaces of the housing; and ii) a second magnetic material member in the impeller, an electromagnet in the first housing member to attract the second magnetic material member, and a position sensor mounted in the first housing member to detect a position of the impeller.

With the blood pump apparatus disclosed here, the impeller can be rotated without contacting the inner surface of the housing, and can be rotated in a favorable manner without being influenced by the material used to form the housing.

BRIEF DESCRIPTION OF THE DRAWING FIGURES

DETAILED DESCRIPTION

Figure 2:
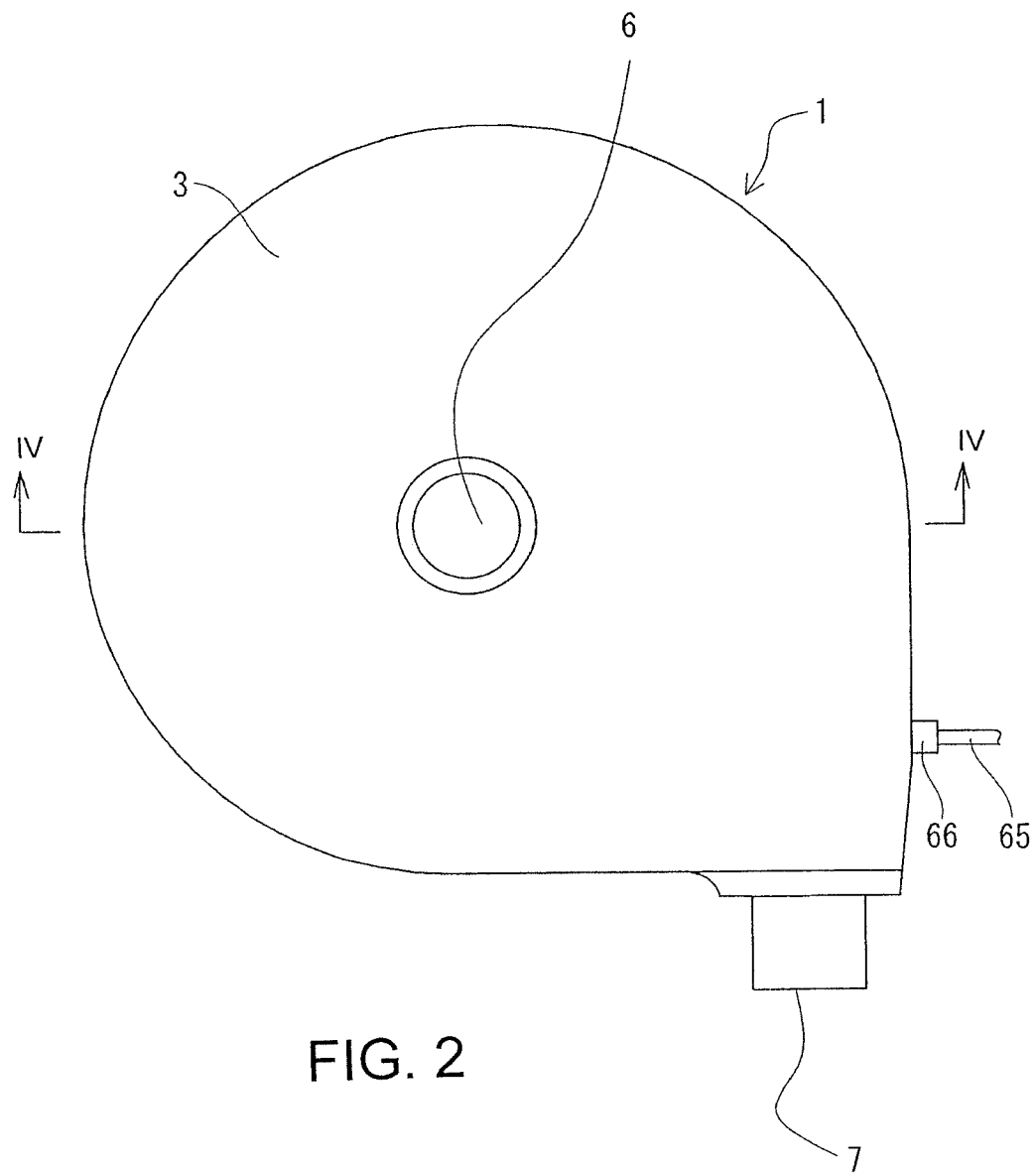
FIG. 2 is a plan view of the blood pump apparatus shown in FIG. 1.
Figure 3:
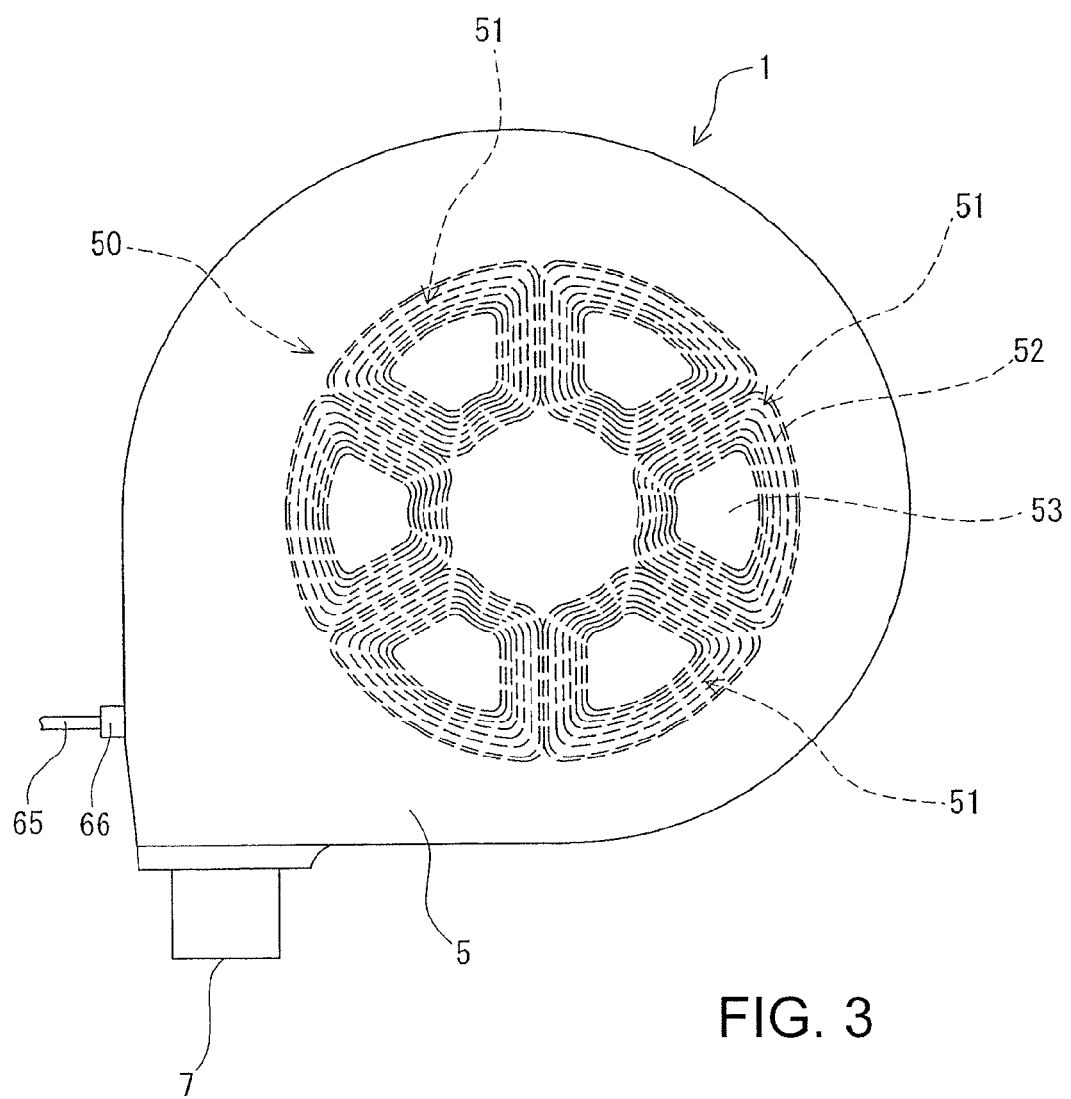
FIG. 3 is a bottom view of the blood pump apparatus shown in FIG. 1.
Figure 4:
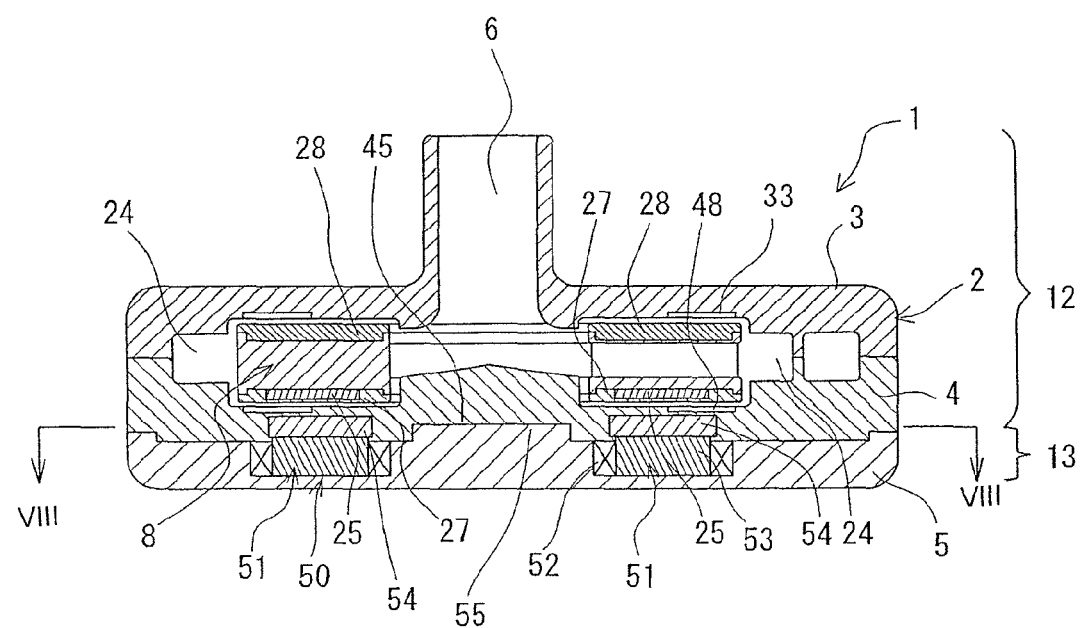
FIG. 4 is a cross-sectional view of the blood pump apparatus taken along the section line IV-IV in FIG. 2.

The embodiment of the blood pump apparatus 1 shown in FIGS. 1-8 includes: a housing 2 having a blood inlet port 6 and a blood outlet port 7; a pump unit 12 specifically shown in FIG. 4 including an impeller 8 which has a plurality of magnetic materials (magnetic material bodies or pieces) 25 and which rotates within the housing to feed blood; and an impeller rotational torque generation section 13 for rotating the impeller. The housing 2 includes a plurality of magnetic members 54 embedded between the impeller 8 and the impeller rotational torque generation section 13 for transmitting a magnetically attractive force generated by the impeller rotational torque generation section 13 to the magnetic material bodies 25 of the impeller. The magnetic material bodies 54 are embedded in the housing 2 (second housing member 4) so that the magnetic material bodies 54 are positioned in respective recesses in the housing 2 (second housing member 4) and so that the magnetic material bodies 54 form a part of the housing 2 or second housing member 4 (e.g., the material forming the second housing member 4 contacts and surrounds at least a portion of the magnetic material bodies 54 as shown in FIG. 4). The blood pump apparatus 1 includes a non-contact bearing mechanism for rotating the impeller without contacting within the housing when the impeller is rotated by the impeller rotational torque generation section 13.

The blood pump apparatus 1 in the present embodiment includes the housing 2, the pump unit 12 composed of the impeller 8 accommodated in the housing 2, and the impeller rotational torque generation section 13 for rotating the impeller. In addition, in the blood pump apparatus 1 in the present embodiment, the impeller rotational torque generation section 13 is attachable to and detachable from the pump unit 12. With the impeller rotational torque generation section 13 thus attachable to and detachable from the pump unit 12, the impeller rotational torque generation section 13 having no blood contact part during use can be reused, so that only the pump unit 12 which has a blood circulating part is disposable.

Figure 1:
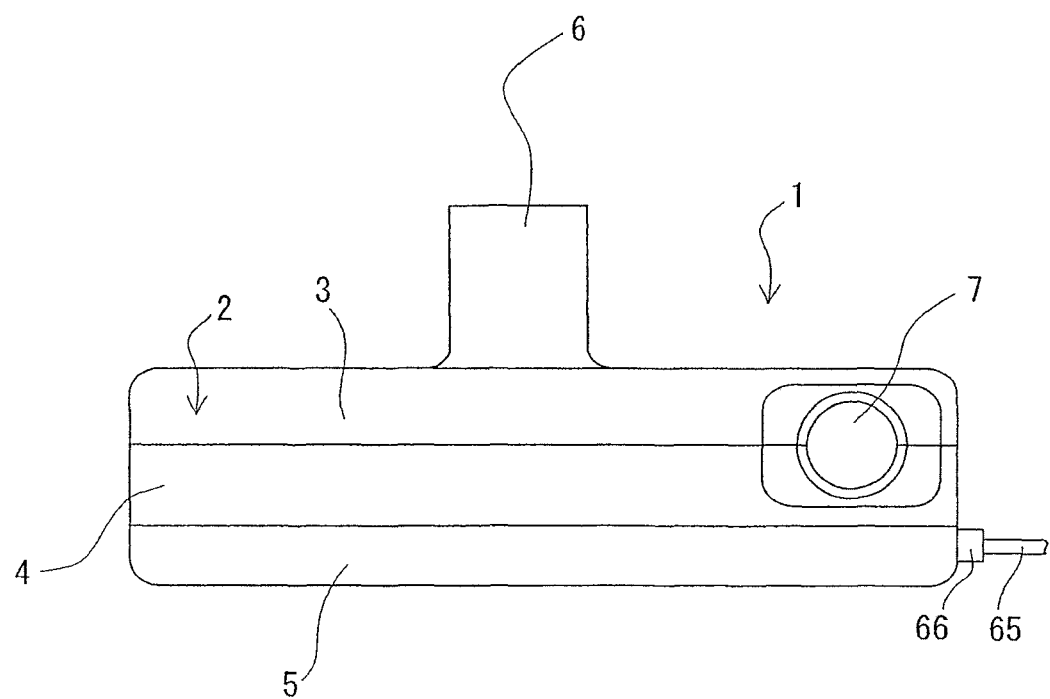
FIG. 1 is a front view of an embodiment of the blood pump apparatus disclosed here.

The housing 2 includes: a first housing member 3 having the blood inlet port 6 and a recess for accommodating an upper portion of the impeller 8; and a second housing member 4 having the blood outlet port 7 and a recess for accommodating a lower portion of the impeller 8. The housing 2 is formed by combining the first housing member 3 and the second housing member 4 with each other. The interior of the housing 2 is provided with or forms a blood chamber 24 through which the blood inlet port 6 and the blood outlet port 7 communicate with each other. As shown in FIGS. 1 and 2, the blood inlet port 6 projects substantially perpendicularly from around the center of the upper surface of the housing 2 (the first housing member 3). The blood inlet port 6 is not limited to the straight pipe as illustrated, but may be a curved pipe or a bent pipe. As shown in FIGS. 1 to 7, the blood outlet port 7 projects in a tangential direction from the side surface of the housing 2, which is formed in a substantially hollow cylindrical shape. According to this disclosed embodiment, the blood outflow passage is of a double volute structure divided into two parts in the, but it may be of a single volute structure or of a voluteless structure.

The housing 2 includes the plurality of magnetic members 54 embedded between the impeller 8 and the impeller rotational torque generation section 13 for transmitting a magnetically attractive force generated by the impeller rotational torque generation section 13 to the magnetic material bodies 25 of the impeller. Specifically, the plurality of magnetic members 54 are embedded in the second housing member 4 (more specifically, in the bottom wall of the second housing member 4). It is particularly preferable that the magnetic members 54 are so embedded as not to be exposed to the inside of the blood chamber 24, as in the pump apparatus 1 according to the present embodiment. As the magnetic member 54, a ferromagnetic material is used. The magnetic member 54 is preferably a soft magnetic material. Examples of the soft magnetic material usable here include flat rolled magnetic steel sheets and strips (silicon steel plates), pure iron, carbon steels containing up to 0.3 wt. % of carbon (for example, low carbon steel designated as 515C in JIS), and ferritic stainless steels (specifically, SUSXM27 in JIS).

The housing 2, specifically the first housing member 3 and the second housing member 4, are formed of synthetic resin or metal. Examples of the material for forming the housing 2 include synthetic resins, particularly, thermoplastic hard synthetic resins such as polycarbonate, acrylic resins [polyacrylates (e.g., polymethyl methacrylate, polymethyl acrylate), polyacrylamide, acrylonitrile-styrene copolymer, acrylonitrile-butadiene-styrene copolymer, etc.], polyolefins (polyethylene, polypropylene, ethylene-propylene copolymer, ultra-high-molecular-weight polyethylene), and styrene resins [polystyrene, MS resin (methacrylate-styrene copolymer), MBS resin (methacrylate-butylene-styrene copolymer)]. Particularly preferred are polycarbonate, polymethyl acrylate, and ultra-high-molecular-weight polyethylene. Examples of the metal which can be used here include titanium, titanium alloys, and stainless steels. Particularly preferred are titanium and titanium alloys.

In addition, the first housing member 3 and the second housing member 4 have peripheral parts which make surface contact with each other, as shown in FIG. 4. In the case of a synthetic resin-made housing, these peripheral parts are joined together in a liquid-tight fashion by microwave, ultrasonic or other heat fusing, adhesion with an adhesive, or the like. In the case of a metallic housing, these peripheral parts are joined together in a liquid-tight fashion by welding, screwing with a seal member sandwiched therebetween, or the like.

The impeller 8 is contained in the housing 2. Specifically, as shown in FIG. 4, a disk-shaped impeller 8 provided with a centrally located through-hole is contained in the blood chamber 24 formed inside the housing 2.

Figure 5:
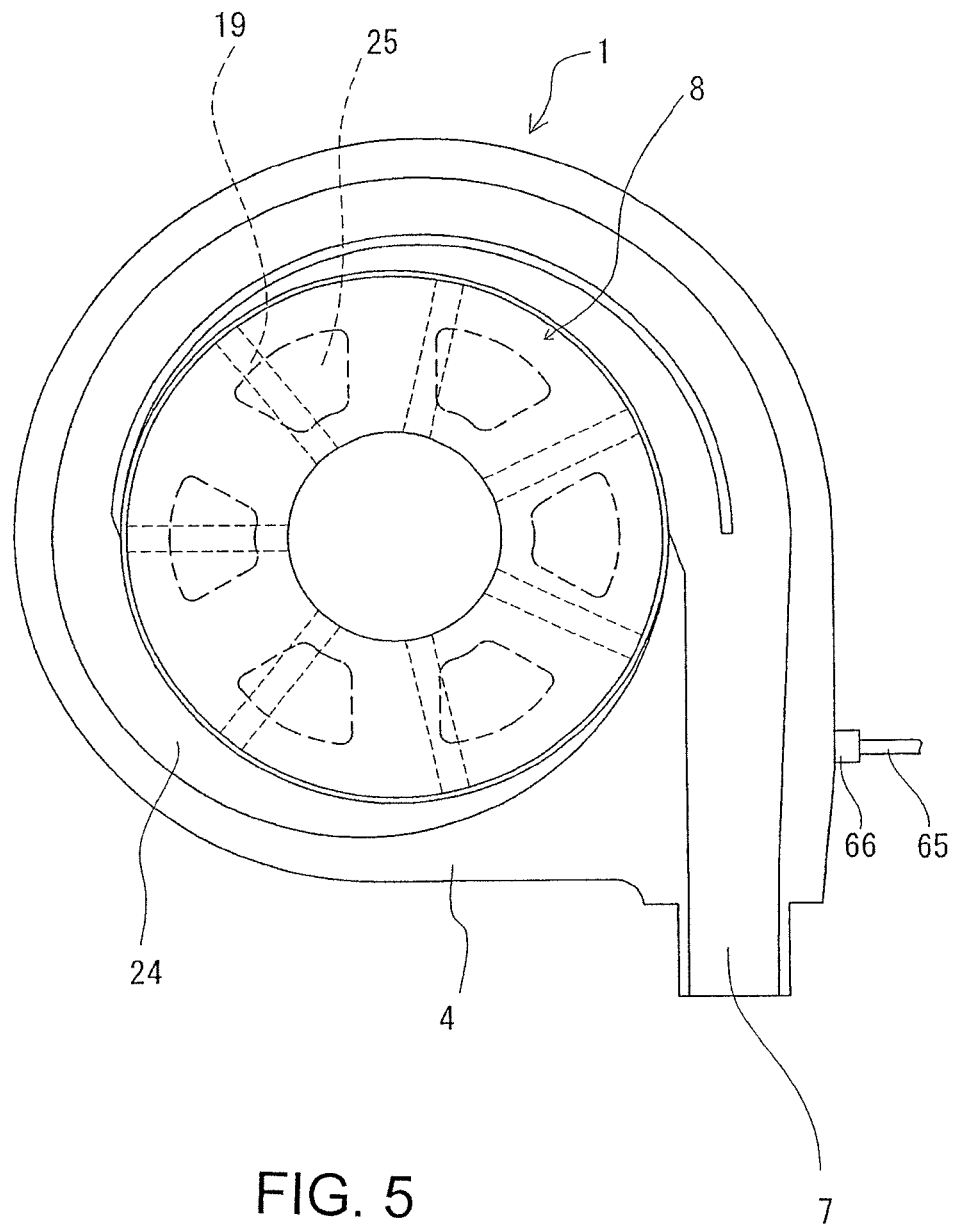
FIG. 5 is a plan view of the blood pump apparatus shown in FIG. 1 illustrating a condition where the first housing member has been removed.

As shown in FIGS. 4 and 5, the impeller 8 includes an annular member (lower shroud) 27 forming a lower surface, an annular member (upper shroud) 28 provided with an opening in its center and forming an upper surface, and a plurality of (for example, seven) vanes 19 between the two members or shrouds. Between the lower shroud and the upper shroud, there are formed a plurality of (for example, seven) blood flow channels, each partitioned by the adjacent vanes 19. As shown in FIG. 5, the blood flow channels communicate with the central opening of the impeller 8, and extend to the outer peripheral edge while gradually increasing in width, starting from the central opening of the impeller 8. In other words, the vanes 19 are each formed between the adjacent blood flow channels. In the present embodiment, the blood flow channels and the vanes 19 are provided at regular angular intervals and in substantially the same shape, respectively.

As shown in FIG. 4, the impeller 8 has a plurality of (for example, six) magnetic material bodies or pieces 25 (permanent magnets; driven magnets) embedded therein. In the present embodiment, the magnetic material bodies 25 are embedded in the lower shroud 27. The magnetic material bodies 25 (permanent magnets) thus embedded are attracted toward the impeller rotational torque generation section 13 side by stators 51 of the impeller rotational torque generation section 13 and, also, receive a rotation torque of the impeller rotational torque generation section 13 through the magnetic members embedded in the housing 2 (the second housing member 4).

In addition, where a certain number of magnetic bodies 25 are embedded as in the present embodiment, magnetic coupling with the plurality of stators 51 which will be described later can be secured sufficiently. Preferred shapes of the magnetic material bodies 25 (permanent magnet) include a circle, a sector and, further, a ring (an integral form in which N poles and S poles are alternately polarized). The impeller members are formed of a highly corrosion-resistant metal (titanium, stainless steel SUS316L, or the like) or synthetic resin. As the synthetic resin here, those which have been described above as material for the housing can be preferably used.

The blood pump apparatus 1 disclosed here includes a non-contact bearing mechanism for rotating the impeller without contacting the inner surface of the housing when the impeller is rotated by the impeller rotational torque generation section 13.

Figure 6:
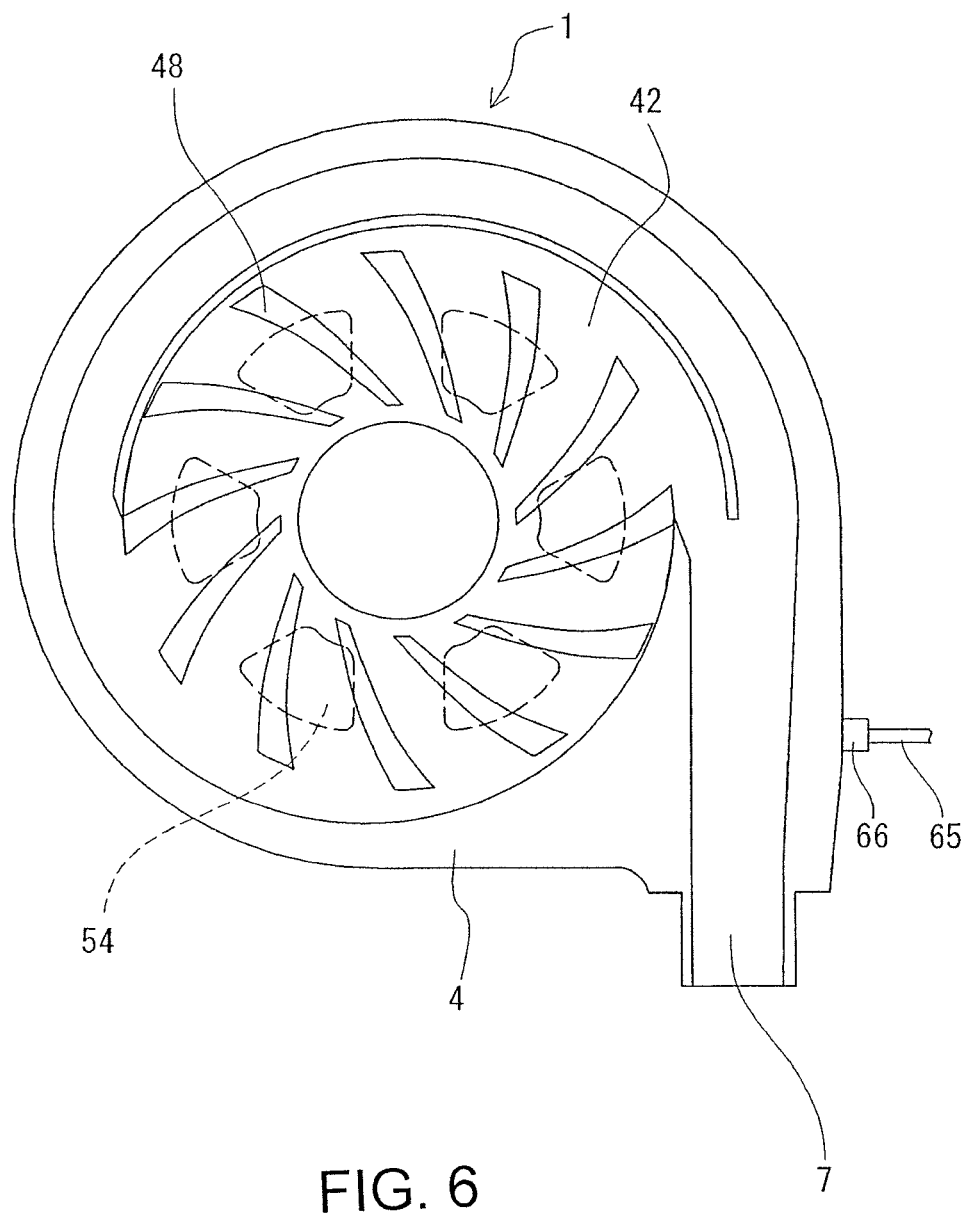
FIG. 6 is a plan view of the second housing member of the blood pump apparatus shown in FIG. 1.

In the pump apparatus 1 disclosed here, the non-contact bearing mechanism is composed of grooves for hydrodynamic bearing 48 provided in the inner surface of the housing 2 on the impeller rotational torque generation section 13 side, in other words in a surface (bottom wall surface) of the recess in the second housing member 4. The impeller is rotated, without contact, under a dynamic pressure bearing effect offered by a dynamic pressure generated between a surface (groove for hydrodynamic bearing formed part) 42 in which the grooves for hydrodynamic bearing 48 are formed and the impeller 8, by rotation thereof at a rotating speed of not less than a predetermined value. As shown in FIG. 6, the groove for hydrodynamic bearing formed part 42 is formed in a size corresponding to a bottom surface (a surface on the impeller rotational torque generation section side) of the impeller 8. In the pump apparatus 1 disclosed here, each of the grooves for hydrodynamic bearing 48 has its one end on the peripheral edge (circumference) of a circular part slightly outwardly spaced from the center of the surface of the recess in the second housing member, and extends therefrom nearly to the outer edge of the recess surface in a vortex form (in other words, in a curved form) while gradually increasing in width. The grooves for hydrodynamic bearing 48 are plural in number, are the same shape (inclusive of substantially the same shape), and are arranged at regular (equal) intervals (inclusive of substantially equal intervals). The grooves for hydrodynamic bearing 48 are each a recess, the depth of which is preferably about 0.005 to 0.4 mm. The number of the grooves for hydrodynamic bearing 48 is preferably about 6 to 36. In the present example, twelve grooves for hydrodynamic bearing are arranged at regular (equal) angular intervals about the center axis of the impeller. The grooves for hydrodynamic bearing 48 in the pump apparatus disclosed here have a so-called inward spiral groove shape. In the process of pumping fluid by the action of the groove for hydrodynamic bearing formed part 42, clockwise rotation of the impeller raises the pressure from the outer diameter side toward the inner diameter side of the groove part, so that a force in the opposite direction is obtained between the impeller 8 and the housing 2 forming the groove for hydrodynamic bearing formed part, and this force serves as a dynamic pressure.

The impeller 8 is attracted toward the impeller rotational torque generation section 13 side at the time of rotation. The presence of the groove for hydrodynamic bearing formed part as above-mentioned helps ensure that, by the dynamic pressure bearing effect provided between the groove for hydrodynamic bearing formed part 42 of the housing and the bottom surface of the impeller 8 (or between the groove for hydrodynamic bearing formed part of the impeller and the housing inner surface), the impeller 8 is separated from the housing inner surface, and is rotated without contact, whereby a blood flow channel is secured between the lower surface of the impeller and the housing inner surface, and blood stagnation between these surfaces and the resultant thrombus formation are prevented from occurring. Further, in a normal condition, the groove for hydrodynamic bearing formed part exhibits a stirring action between the lower surface of the impeller and the housing inner surface, so that partial blood stagnation between these surfaces is inhibited or prevented from occurring.

Furthermore, with respect to the grooves for hydrodynamic bearing 48, corner portions are preferably rounded so as to have a radius of curvature R of at least 0.05 mm. This helps ensure better suppression of hemolysis generation.

The groove for hydrodynamic bearing formed part may be provided in that surface of the impeller 8 which is on the impeller rotational torque generation section side, not on the housing side. In this case, also, the same configuration as that of the groove for hydrodynamic bearing formed part described above is preferably adopted. Specifically, the grooves for hydrodynamic bearing may be provided in that surface of the impeller 8 which is on the impeller rotational torque generation section 13 side (in other words, in the bottom surface of the impeller 8).

The pump apparatus 1 in the present embodiment can be constructed so that the housing inner surface on the opposite side to the impeller rotational torque generating part side (i.e., the surface of the recess in the first housing member 3) may also be provided with a groove for hydrodynamic bearing formed part (second groove for hydrodynamic bearing formed part) 32 having a plurality of grooves for hydrodynamic bearing (second grooves for hydrodynamic bearing) 33.

The impeller 8 is rotated without contact under the dynamic pressure bearing effect produced between the groove for hydrodynamic bearing formed part 42 and the impeller 8 by rotation of the impeller at a rotating speed of not less than a predetermined value. The second grooves for hydrodynamic bearing 33 prevent the impeller from making close contact with the surface of the recess in the first housing member when an external impact is exerted or when the dynamic pressure produced by the groove for hydrodynamic bearing formed part 42 is raised excessively. The dynamic pressure generated by the groove for hydrodynamic bearing formed part 42 and the dynamic pressure generated by the second groove for hydrodynamic bearing formed part 32 may be different from each other.

Figure 7:
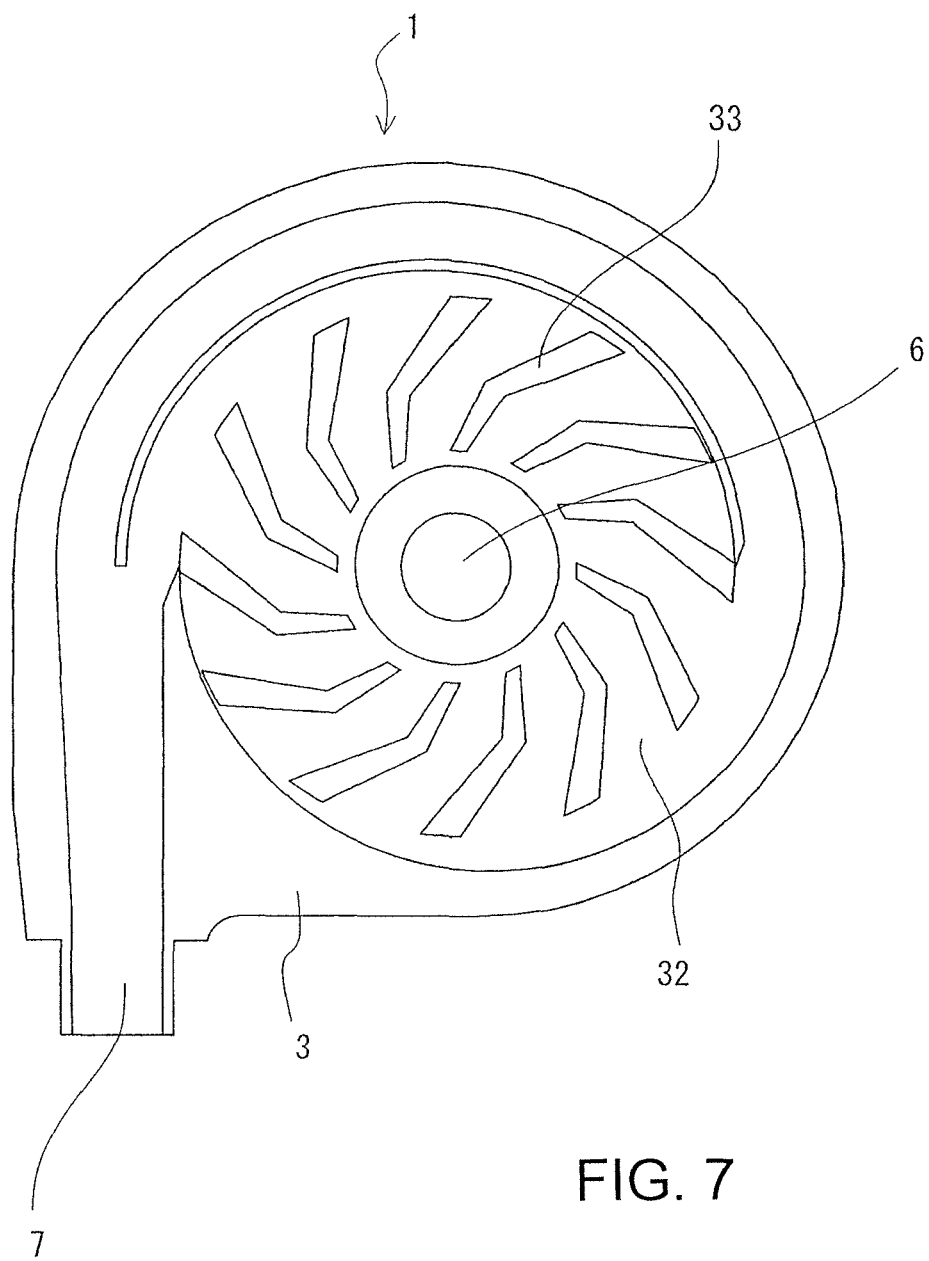
FIG. 7 is a bottom view of the first housing member of the blood pump apparatus shown in FIG. 1.

As shown in FIGS. 4-7, the groove for hydrodynamic bearing formed part 32 possesses a size corresponding to the upper surface (the surface on the opposite side to the impeller rotational torque generation section 13) of the impeller 8. As shown in FIG. 7, each of the grooves for hydrodynamic bearing 33 has its one end on the peripheral edge (circumference) of a circular part slightly spaced from the center of the groove for hydrodynamic bearing formed part 32 (in other words, the center of the inner surface of the recess in the first housing member 3), and extends therefrom nearly to the outer edge of the recess in a vortex form (i.e., in a curved form) while gradually increasing in width. In the present embodiment, the groove for hydrodynamic bearing has a so-called herringbone shape which is bent in an intermediate portion of the groove. A plurality of the grooves for hydrodynamic bearing 33 are provided, the plural grooves for hydrodynamic bearing 33 possess the same shape (inclusive of substantially the same shape), and are arranged at equal or regular intervals (inclusive of substantially equal intervals). The grooves for hydrodynamic bearing 33 are each in the form of a recess, the depth of which is preferably about 0.005 to 0.4 mm. The number of grooves for hydrodynamic bearing 33 is preferably 6 to 36. In the present embodiment, twelve grooves for hydrodynamic bearing are arranged at regular or equal angular intervals about the center axis of the impeller.

The grooves for hydrodynamic bearing 33 possess corner portions that are preferably rounded so as to have a radius of curvature R of at least 0.05 mm. This helps ensure that generation of hemolysis and thrombus formation can be more suppressed.

The second groove for hydrodynamic bearing formed part may be provided in that surface of the impeller 8 which is on the opposite side to the impeller rotational torque generation section side (i.e., the upper surface of the impeller 8 which faces away from the impeller rotational torque generation section), not on the housing side. In this case, the same configuration as that of the second groove for hydrodynamic bearing formed part described above is preferably adopted. In addition, the blood pump apparatus 1 disclosed here includes the impeller rotational torque generation section 13 for rotating the impeller. In the blood pump apparatus 1 in the present embodiment, the impeller rotational torque generation section 13 is attachable to and detachable from the pump unit 12.

Figure 8:
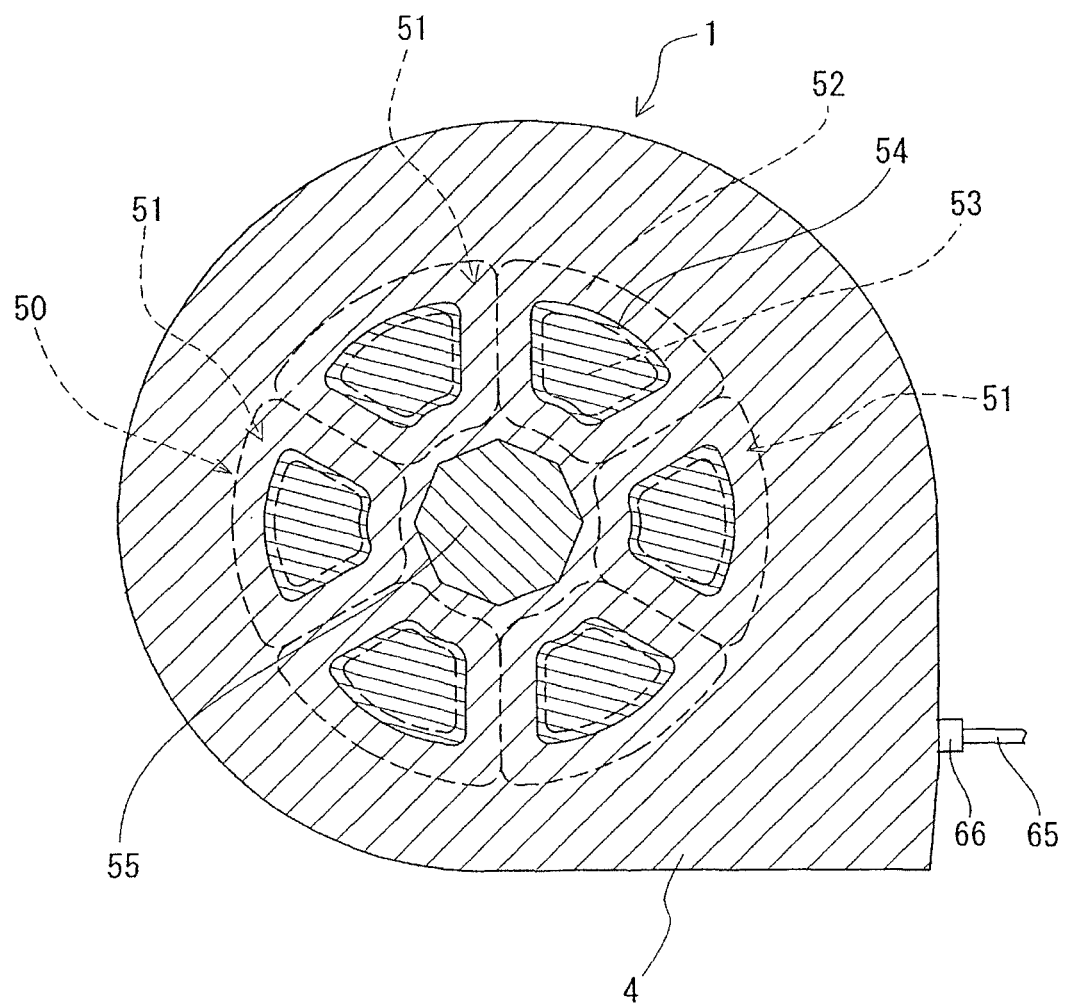
FIG. 8 is a cross-sectional view taken along the line VIII-VIII in FIG. 4.

The impeller rotational torque generation section 13 of the blood pump apparatus 1 according to the present embodiment, as shown in FIGS. 3, 4 and 8, is composed of a motor stator 50 including a plurality of stators 51 disposed on the circumference of a circle (arranged in an annular form). A third housing member 5 is provided with an annular recess (doughnut-shaped recess), and the plurality of stators 51 are contained in the third housing member 5, in the state of being arranged in an annular pattern (doughnut-like pattern). The stator 51 has a stator core 53 and a stator coil 52 wound around the stator core 53. In the pump apparatus 1 according to the present embodiment, six stators 51 form the stator motor 50. As the stator coil 52, a multilayer wound stator coil is used. With the direction of current flowing in the stator coils 52 of the respective stators 51 switched over or alternating a rotating magnetic field is generated, by which the impeller is attracted and rotated.

The side surface of the third housing member 5 is provided with a cable port 66. As shown in FIGS. 1, 3, 5, 6 and 8, the cable port 66 is formed at the side surface of the third housing member 5. Cords connected to the stator coils 52 of the respective stators 51 are bundled, and, for example, a reinforcement member is wound around the outer layer of the bundle, to form a cable 65. The cable 65 extends to the outside via the cable port 66.

In the blood pump apparatus 1 in the present embodiment, as shown in FIGS. 4 and 8, the respective magnetic members 54 of the housing 2 (specifically, the second housing member 4) are so disposed as to be located on, or in overlying relation to, the stator cores 53 of the respective stators 51 described above. That is, each of the plurality of magnetic members 54 is positioned in circumferential alignment with one of the stator cores 53 of the stators 51. The stator cores 53 in the present embodiment are each sector-shaped as shown in FIG. 8, and correspondingly, the magnetic members 54 are also each sector-shaped. The magnetic members 54 are slightly greater in size than the stator cores 53.

Further, in the blood pump apparatus 1 according to the present embodiment, as shown in FIGS. 4 and 8, each of the magnetic members 54 of the housing 2 (specifically, the second housing member 4) makes direct contact with the stator core 53 of each of the stators 51. More specifically, in this pump apparatus 1, an upper end portion of the stator core 53 projects upwardly slightly beyond the stator coil 52, and the projecting portion is exposed. The magnetic member 54 is so embedded in the second housing member 4 that its lower surface is exposed; further, the portion where the lower surface of the magnetic member 54 is exposed forms a recess in which the projecting portion of the stator core 53 is accommodated. Therefore, the magnetic member 54 and the stator core 53 are in contact with each other. This helps ensure that a magnetic force generated in the stator 51 can be securely transmitted to the magnetic member 54.

In the pump apparatus 1 according to the present embodiment, the pump unit 12 and the impeller rotational torque generation section 13 can be attached to and detached from each other, and both of them have a connecting mechanism. In the pump apparatus 1 in the present embodiment, the second housing member of the pump unit 12 is provided at its bottom surface with a first engaging part (a recess) 45, whereas the housing 5 of the impeller rotational torque generation section 13 is provided with a second engaging part (specifically, a projection) 55 which engages the first engaging part (recess) 45. The engagement between the first engaging part (recess) 45 of the pump unit 12 and the second engaging part (projection) 55 of the impeller rotational torque generation section 13 connects the units to each other. In addition, the first engaging part (recess) 45 and the second engaging part (projection) 55 of the impeller rotational torque generation section 13 are preferably provided with a positioning mechanism as shown in FIG. 8. In the configuration shown in FIG. 8, the first engaging part (recess) 45 and the second engaging part (projection) 55 of the impeller rotational torque generation section 13 have shapes (specifically, polygonal shapes in section) corresponding to each other so as to enable positioning. In the condition where these engaging parts are engaged with each other, each magnetic member 54 of the pump unit 12 is positioned over the stator core 53 of a respective stator 51, and further, each magnetic member 54 and the stator core 53 are in contact with each other. The sectional shapes of the first engaging part (recess) 45 and the second engaging part (projection) 55 of the impeller rotational torque generation section 13 are not limited to polygonal shapes, but may be elliptic shapes, star shapes or the like. The manner of engagement between the first engaging part of the pump unit 12 and the second engaging part of the impeller rotational torque generation section 13 is not limited to the above-mentioned one. As in a pump in an embodiment shown in FIG. 15, the first engaging part 46 may be a projection and the second engaging part 56 may be a recess.

Figure 9:
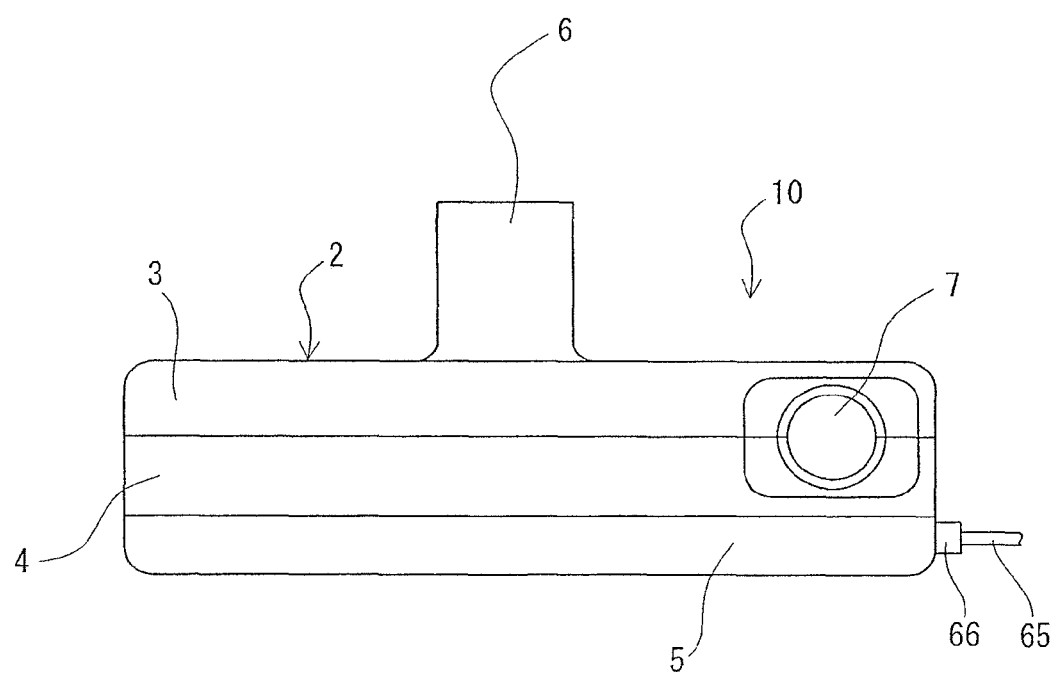
FIG. 9 is a front view of another embodiment of the blood pump apparatus disclosed here.
Figure 10:
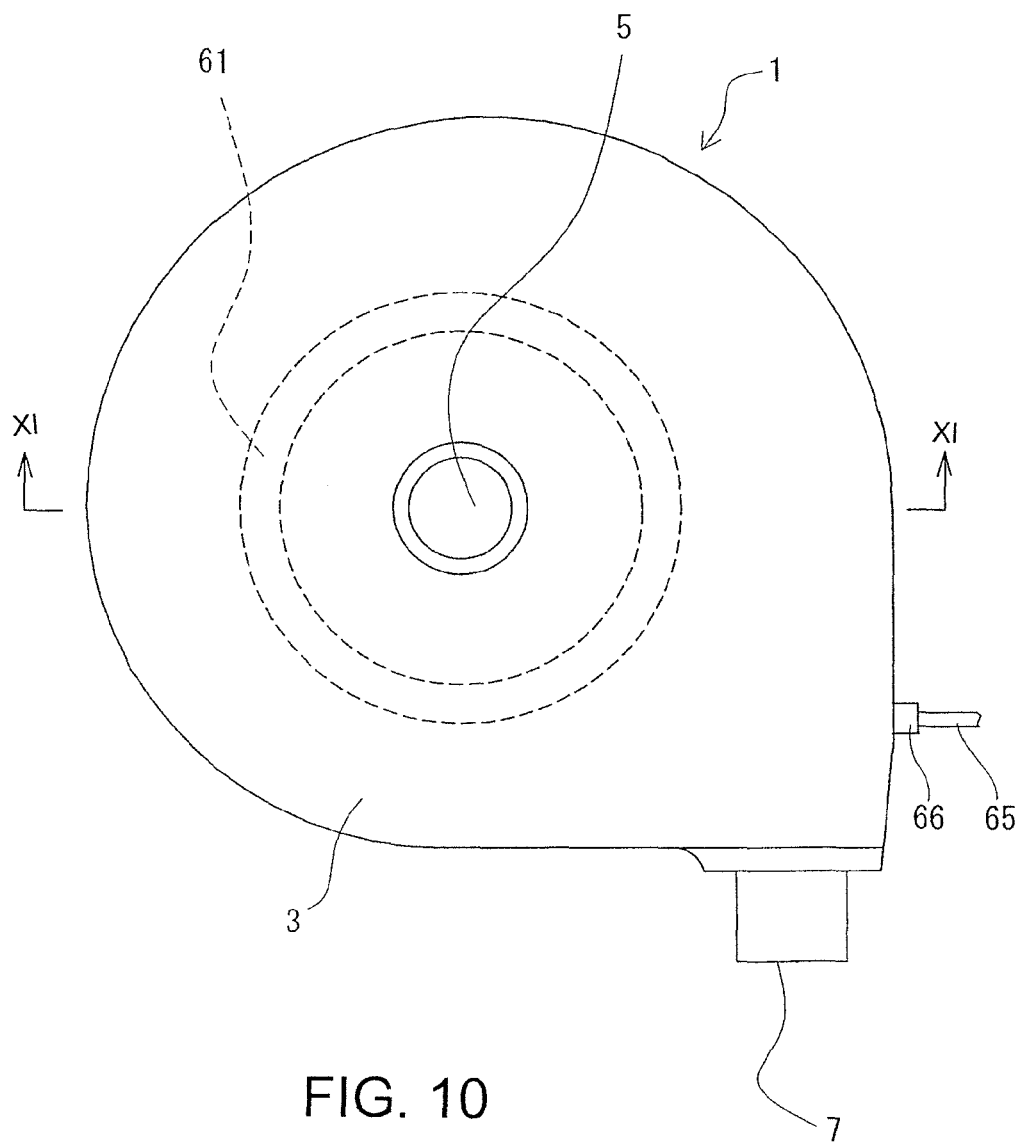
FIG. 10 is a plan view of the blood pump apparatus shown in FIG. 9.
Figure 11:
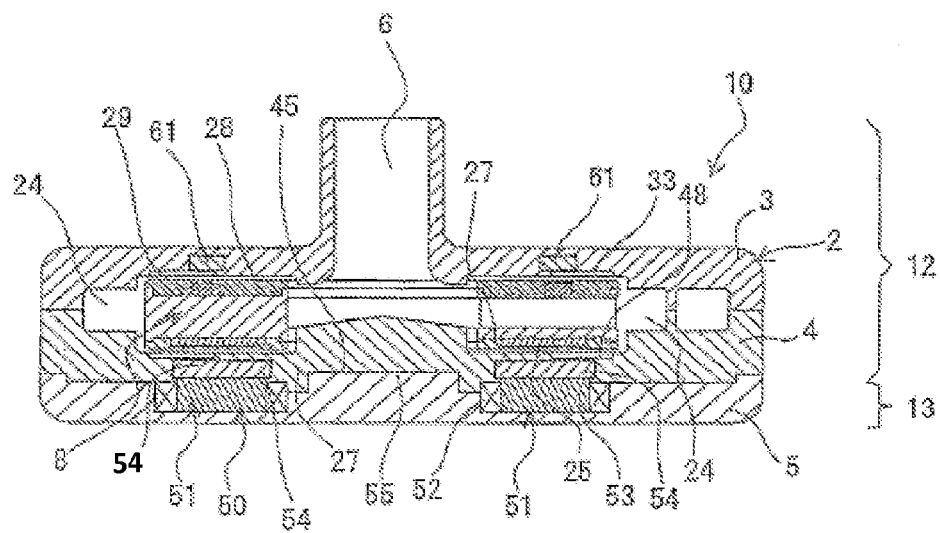
FIG. 11 is a cross-sectional view of the blood pump apparatus taken along the section line XI-XI in FIG. 10.

Another version of the blood pump apparatus disclosed here is illustrated in FIGS. 9 to 11. The blood pump apparatus 10 in the present embodiment differs from the blood pump apparatus 1 in the above-described embodiment in that the impeller 8 includes a second magnetic material (magnetic material body or piece) 29 and the blood pump apparatus includes a permanent magnet 61, in the housing on the opposite side to the impeller rotational torque generation section 13 side (specifically, in the first housing member 3), for attracting the second magnetic material body 29 of the impeller 8. The other aspects and features of the two blood pump apparatuses are the same. Those parts of the blood pump apparatus which are the same as those described above are identified by common reference numerals and a detailed description of such features is not repeated.

In the blood pump apparatus 10 according to the present embodiment, as shown in FIG. 11, second magnetic material 29 is embedded in the impeller 8 in an annular member (upper shroud) 28 provided with an opening in its center and forming an upper surface. The second magnetic material 29 is preferably a flat-plate annular member. The second magnetic material 29 is disposed at such a position as to be slightly inwardly of the peripheral edge portion of the impeller 8. The second magnetic material 29 is preferably a permanent magnet or a ferromagnetic material, particularly preferably a permanent magnet.

As shown in FIGS. 10 and 11, the permanent magnet 61 for attracting the second magnetic material 29 of the impeller 8 is embedded in the first housing member 3 so as to be located on the upper side, or in overlying relation to, the second magnetic material 29 of the impeller 8. The permanent magnet 61 is preferably ring-shaped so as to correspond in shape to, or be the same shape as, the second magnetic material 29, as shown in FIG. 10.

In the pump apparatus 10 in the present embodiment, a housing inner surface on the opposite side to the impeller rotational torque generation section side (in other words, the surface of the recess in the first housing member 3) is also provided with a groove for hydrodynamic bearing formed part (second groove for hydrodynamic bearing formed part) 32 having a plurality of grooves for hydrodynamic bearing (second grooves for hydrodynamic bearing) 33. Therefore, a dynamic pressure produced between the groove for hydrodynamic bearing formed part 32 and the impeller 8, by rotation of the impeller 8 at a rotating speed of not less than a predetermined value, opposes an attraction force between the second magnetic material 29 of the impeller 8 and the permanent magnet 61. This helps ensure that the impeller 8 is prevented from making close contact with the surface of the recess in the first housing member, and the impeller is kept in favorable rotation without contacting the housing inner surface. The permanent magnet 61 and the second magnetic material 29 are not limited to the above-mentioned ring-shaped permanent magnets, but may be ones in which a plurality of permanent magnets and a plurality of second magnetic materials are disposed on the circumferences of circles substantially at regular angular intervals, respectively. In this case, the number of permanent magnets and the number of second magnetic material members is preferably 2 to 8, particularly 3 to 6. In addition, the component for attracting the second magnetic material 29 toward the opposite side to the direction of attraction of the impeller rotational torque generation section may be an electromagnet, instead of a permanent magnet. In the case where an electromagnet is used, a plurality of (three) electromagnets are preferably disposed on the circumference of a circle substantially at regular angular intervals, as in a pump apparatus 20 (see FIG. 13) in an embodiment which will be described later.

In the pump apparatus 10 according to the present embodiment, it is preferable that the resultant force of an attraction force for the impeller at the time of generation of a magnetic force by the impeller rotational torque generation section 13 (specifically, an attraction force applied to the impeller through the magnetic members 54) and an attraction force for the impeller by the permanent magnet 61 is balanced in the vicinity of the midpoint of a movable range of the impeller 8 in the housing 2.

In the blood pump apparatus 10 in the present embodiment, also, the side surface of the third housing member 5 has a cable port 66. Specifically, as shown in FIGS. 9 and 10, the cable port 66 is formed at the side surface of the third housing member 5. Cords connected to stator coils 52 of respective stators 51 are bundled, and, for example, a reinforcement member is wound around the outer layer of the bundle to form a cable 65. The cable 65 extends to the outside via the cable port 66.

Figure 12:
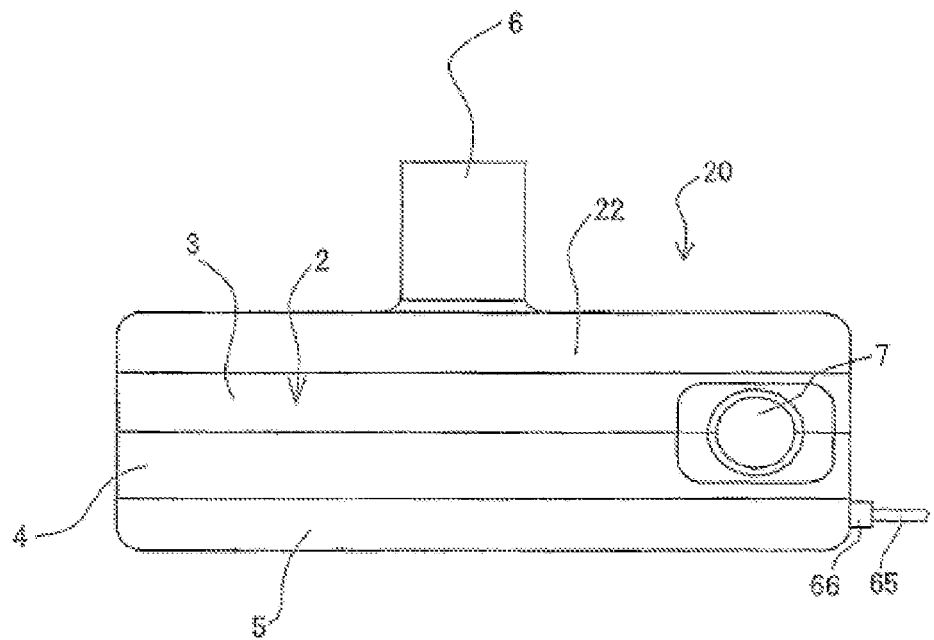
FIG. 12 is a front view of a further embodiment of the blood pump apparatus disclosed here.
Figure 13:
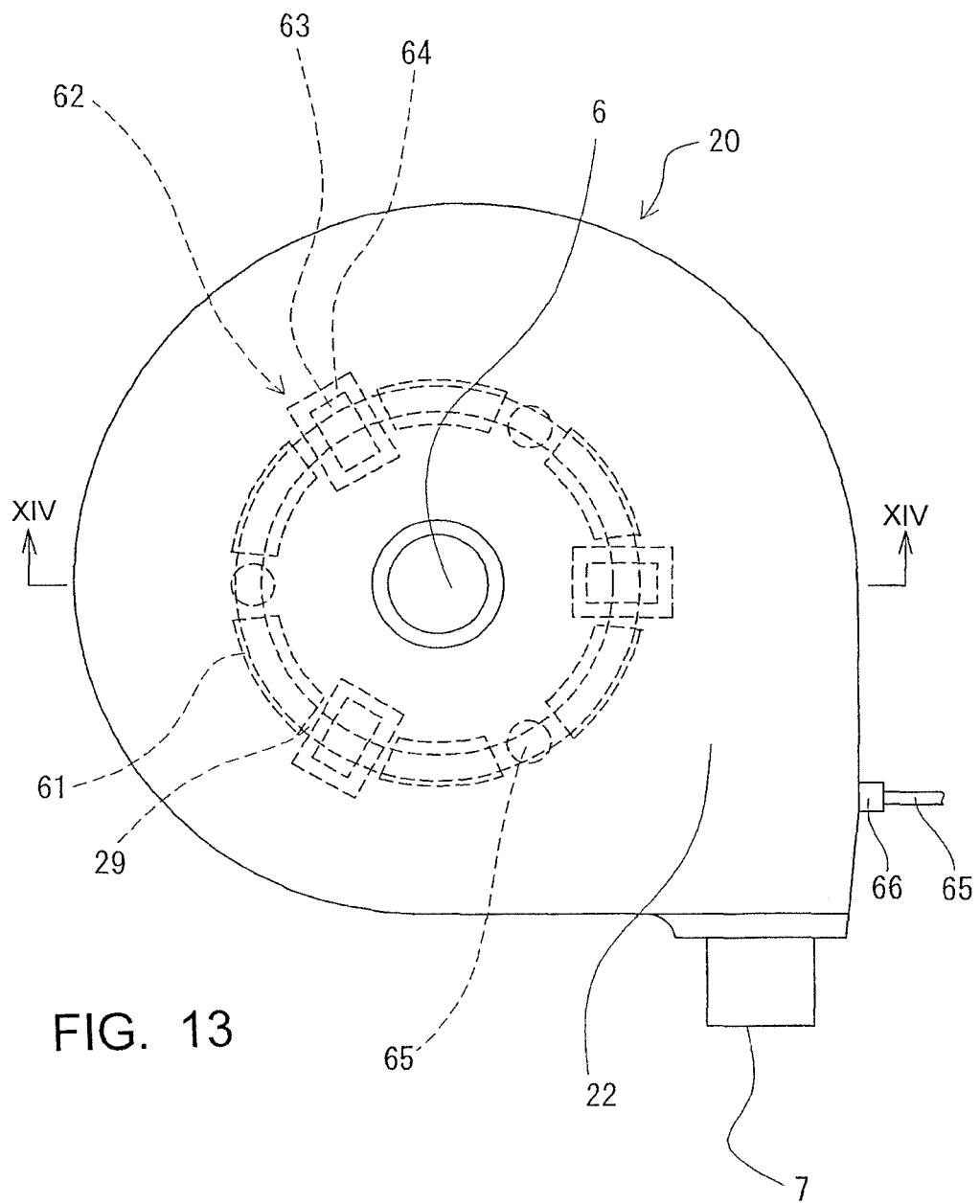
FIG. 13 is a plan view of the blood pump apparatus shown in FIG. 12.
Figure 14:
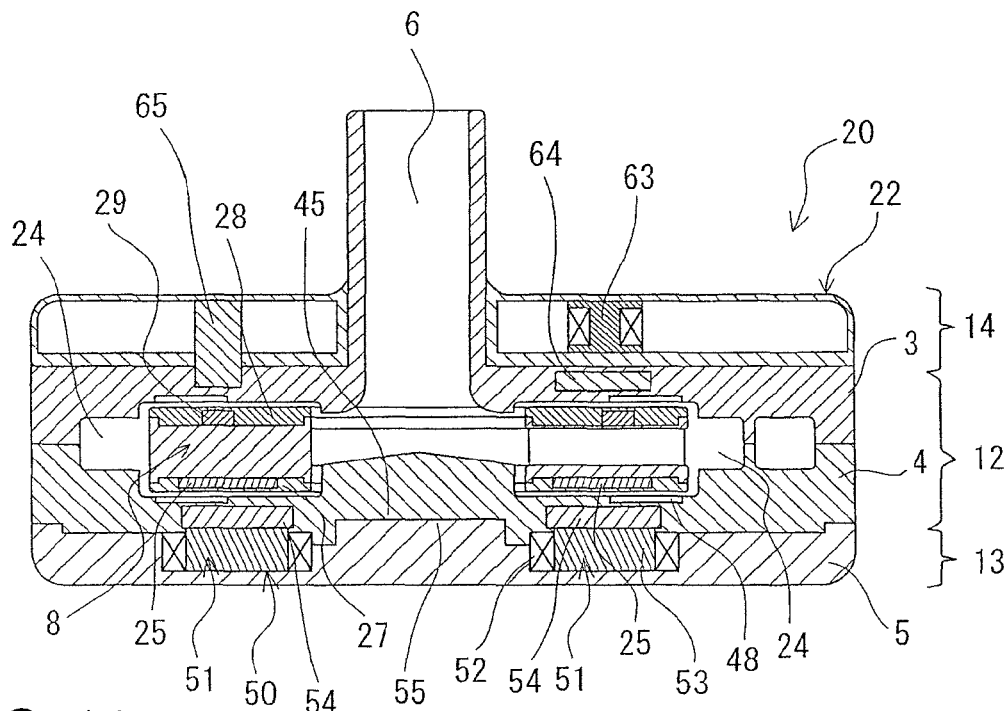
FIG. 14 is a cross-sectional view taken along the section line XIV-XIV in FIG. 13.

Another embodiment of the blood pump apparatus disclosed here is illustrated in FIGS. 12 to 14. The pump apparatus 20 in the present embodiment differs from the above-described pump apparatus 10 only in terms of the non-contact bearing mechanism. Other aspects of the blood pump apparatus are the same as described above and so a detailed description of those other aspects and features, identified by common reference numerals, is not repeated.

In this pump apparatus 20, as shown in FIGS. 13 and 14, a non-contact bearing mechanism (impeller position control unit) 14 includes a plurality of fixed electromagnets 63 for attracting the second magnetic material 29 of the impeller 8, and position sensors 65 for detecting the position of the second magnetic material 29 of the impeller 8. The impeller position control unit 14 includes the plurality of electromagnets 63 contained in an impeller position control unit housing 22, and the plurality of position sensors 65. The plurality of (three) electromagnets 63 and the plurality of (three) position sensors 65 in the impeller position control unit are respectively disposed at respective regular or equal angular intervals. The electromagnets 63 are each composed of a core and a coil. As noted, the number of electromagnets 63 provided in the present embodiment is three, but the number of electromagnets 63 may be more than three; for example four. Three or more electromagnets 63 are provided and the electromagnetic forces thereof are adjusted by use of the results of detection by the position sensors 65, whereby forces in the direction of the rotational axis of the impeller 8 (z-axis) can be balanced, and moments about an x-axis and a y-axis, which are orthogonal to the rotational axis (z-axis), can be controlled. Consequently, the impeller 8 can be rotated without making contact with the housing inner surface.

The position sensor 65 detects the interval or dimension of the gap between the electromagnet 63 and the second magnetic material 29, and the detection output is sent to a control unit of a control mechanism for controlling a current or voltage supplied to the coil of the electromagnet 63.

In the pump apparatus 20 according to the present embodiment, the impeller position control unit 14 is attachable to and detachable from the pump unit 12. As shown in FIGS. 13 and 14, preferably, a plurality of magnetic members 64 each embedded between the impeller 8 and the electromagnet 63 and, further, a plurality of magnetic material members 61 are provided in the first housing member 3 of the pump unit 12, for transmitting magnetically attractive forces generated by the electromagnets 63 to the second magnetic materials 29 of the impeller. Specifically, the plurality of magnetic members 64 and the plurality of the magnetic materials 61 are embedded in the first housing member 3. Particularly, it is preferable that the magnetic members 64 and the magnetic materials 61 are so embedded as not to be exposed to the inside of the blood chamber 24, as in the pump apparatus 20 according to the present embodiment. As the magnetic member 64, a ferromagnetic material is used. A soft magnetic material is preferable. Examples of the soft magnetic material usable here include flat rolled magnetic steel sheets and strips (silicon steel plates), pure iron, carbon steels containing up to 0.3 wt. % of carbon (for example, low carbon steel designated as S15C in JIS), and ferritic stainless steels (specifically, SUSXM27 in JIS). In addition, like in the above-described stator, the core of the electromagnet 63 and the magnetic member 64 embedded in the first housing 3 may make contact with each other. The pump apparatus of this type may not necessarily include the above-mentioned first and second grooves for hydrodynamic bearing.

In addition, in the blood pump apparatus 20 according to the present embodiment, the cable port 66 is provided at the side surface of the third housing member 5. As shown in FIGS. 12 and 13, the cable port 66 is formed at the side surface of the third housing member 5. Cords connected to the stator coils 52 of the respective stators 51, cords connected to the above-mentioned electromagnets and cords connected to the above-mentioned position sensors are bundled, and, for example, a reinforcement member is wound around the outerlayer of the bundle, to form a cable 65. The cable 65 extends to the outside via the cable port 66.

Figure 15:
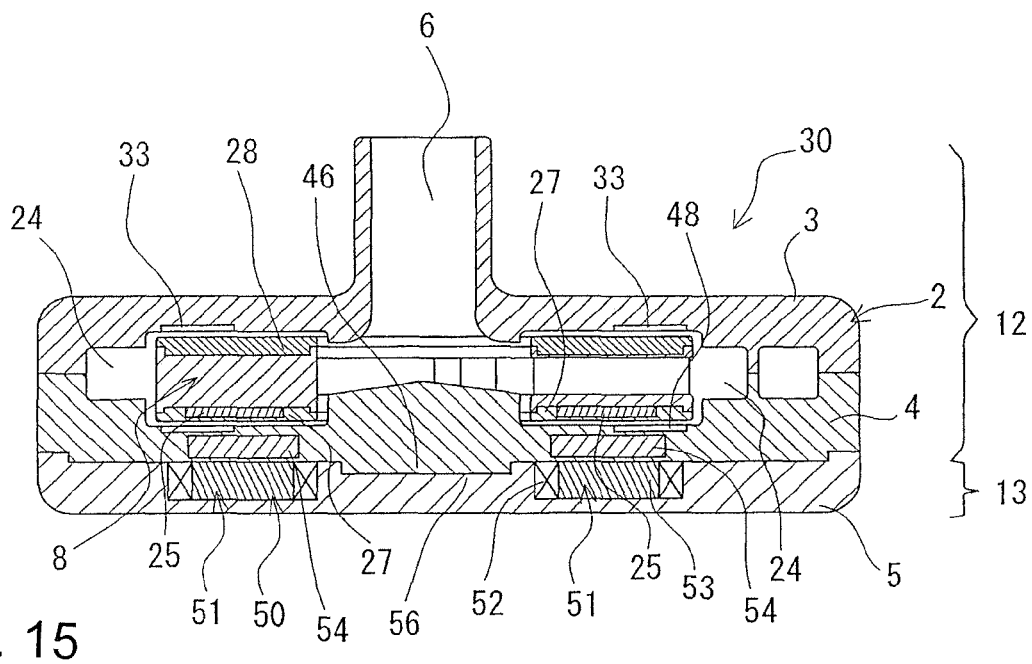
FIG. 15 is a cross-sectional view of yet another embodiment of the blood pump apparatus disclosed here.

In all the above-described embodiments, the magnetic members 54 embedded in the housing 2 (the second housing member 4) may be so configured such that their lower surfaces are not exposed and such that they do not make contact with the stator core 53, as in a pump apparatus 30 according to an embodiment shown in FIG. 15.

The embodiments of the blood pump apparatus disclosed here are applicable both to intracorporeally embedded type pumps and to extracorporeal circulation type pumps. The blood pump apparatus is particularly effective when applied as an extracorporeal circulation type blood pump apparatus.

The blood pump apparatus disclosed includes the housing with blood inlet and outlet ports, a pump unit with the impeller having the plural magnetic material pieces and rotatable within the housing to feed blood, and the impeller rotational torque generation section that rotates the impeller. The housing is provided with the plurality of magnetic members embedded between the impeller and the impeller rotational torque generation section for transmitting a magnetically attractive force generated by the impeller rotational torque generation section to the magnetic material pieces of the impeller. The non-contact bearing mechanism rotates the impeller without contacting the inner surface of the housing when the impeller is rotated by the impeller rotational torque generation section.

By virtue of the housing being constructed so that the blood chamber and the impeller torque generation are separate from each other, the blood pump apparatus can be manufactured and assembled rather easily, and a reduction in weight can be realized. Due to the presence of the plurality of embedded magnetic members, a magnetically attractive force generated by the impeller rotational torque generation section can be securely transmitted to the magnetic materials of the impeller. Further, the blood pump apparatus includes the non-contact bearing mechanism for rotating the impeller without contacting the inner surface of the housing when the impeller is rotated by the impeller rotational torque generation section. This helps enable the impeller to be rotated in the non-contact state.

As discussed above, the impeller rotational torque generation section includes a motor stator in which a plurality of stators are disposed on the circumference of a circle, with the stators each including a stator core and a stator coil wound around the stator core, and the plurality of magnetic members are so disposed as to be located on the stator cores of the stators, respectively. The magnetic members of the housing and the stator cores can be disposed to make contact with each other. Also, the impeller rotational torque generation section can be attachable to and detachable from the pump unit. The magnetic member is preferably a soft magnetic material.

The blood pump apparatus includes a groove for hydrodynamic bearing provided at the inner surface of the housing on the opposite side to the impeller rotational torque generation section side or at the surface of the impeller on the opposite side to the impeller rotational torque generation section side. The impeller includes a second magnetic material, and the blood pump apparatus includes a permanent magnet or electromagnet, for attracting the second magnetic material of the impeller, in the housing on the opposite side to the impeller rotational torque generation section side.

The non-contact bearing mechanism can be composed of a groove for hydrodynamic bearing provided at the inner surface of the housing on the impeller rotational torque generation section side or at the surface of the impeller on the impeller rotational torque generation section side. The non-contact bearing mechanism can also be composed of a second magnetic material provided in the impeller, an electromagnet which is provided in the housing on the opposite side to the impeller rotational torque generation section side and which attracts the second magnetic material of the impeller, and a position sensor for detecting the position of the impeller. The housing can be made of synthetic resin or metal.

The principles, preferred embodiments and other aspects of the blood pump apparatus disclosed here have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A blood pump apparatus comprising:
a housing including a blood inlet port through which blood enters the housing and a blood outlet port through which blood exits the housing;
the housing comprising a first housing member and a second housing member configured so that a blood chamber is formed between the first and second housing members, the blood chamber fluidly communicating with the blood inlet and the blood outlet;
an impeller rotatably positioned in the blood chamber to feed blood, and a plurality of first magnetic material members integrated with the impeller so that the impeller and the plurality of magnetic material members rotate together as a unit within the blood chamber in the housing, the impeller possessing oppositely facing surfaces each of which faces a respective inner surface of the housing;
a motor stator positioned adjacent the housing to generate a magnetically attractive force to rotate the impeller;
a plurality of spaced apart magnetic members each positioned in a respective recess in the second housing member so that the magnetic members are located between the impeller and the motor stator for directly transmitting the magnetically attractive force generated by the motor stator to the magnetic material members of the impeller; and
a non-contact bearing mechanism for rotating the impeller without the impeller contacting the inner surface of the housing when the impeller is rotated by the motor stator, the non-contact bearing mechanism comprising at least one of: i) a plurality of spaced apart grooves provided on at least one of said oppositely facing surfaces of the impeller or at least one of said inner surfaces of the housing; and ii) a second magnetic material member in the impeller, an electromagnet in the first housing member to attract the second magnetic material member, and a position sensor mounted in the first housing member to detect a position of the impeller.

2. The blood pump apparatus according to claim 1, wherein the non-contact bearing mechanism includes the plurality of grooves, and said plurality of grooves are provided on both of said inner surfaces of the housing.

3. The blood pump apparatus according to claim 1, wherein the motor stator includes a plurality of circumferentially positioned stators which each include a stator core and a stator coil wound around the stator core, each of the plurality of magnetic members being positioned in circumferential alignment with a respective one of the stator cores of the stators.

4. The blood pump apparatus according to claim 1, wherein the motor stator is mounted in a third housing member that is attachable to and detachable from the housing.

5. The blood pump apparatus according claim 1, wherein the housing is made of one of synthetic resin and metal.

6. A blood pump apparatus comprising:
a housing including a blood inlet port through which blood enters the housing and a blood outlet port through which blood exits the housing;
the housing comprising a first housing member and a second housing member configured so that a blood chamber is formed between the first and second housing members, the blood chamber fluidly communicating with the blood inlet and the blood outlet;
an impeller rotatably positioned in the blood chamber to feed blood, and a plurality of first magnetic material members integrated with the impeller so that the impeller and the plurality of magnetic material members rotate together as a unit within the blood chamber in the housing, the impeller possessing oppositely facing surfaces each of which faces a respective inner surface of the housing;
a motor stator positioned adjacent the housing to generate a magnetically attractive force to rotate the impeller;
a plurality of spaced apart magnetic members each positioned in a respective recess in the second housing member so that the magnetic members are located between the impeller and the motor stator for directly transmitting the magnetically attractive force generated by the motor stator to the magnetic material members of the impeller;
a non-contact bearing mechanism for rotating the impeller without the impeller contacting the inner surface of the housing when the impeller is rotated by the motor stator, the non-contact bearing mechanism comprising at least one of: i) a plurality of spaced apart grooves provided on at least one of said oppositely facing surfaces of the impeller or at least one of said inner surfaces of the housing; and ii) a second magnetic material member in the impeller, an electromagnet in the first housing member to attract the second magnetic material member, and a position sensor mounted in the first housing member to detect a position of the impeller;
wherein the motor stator includes a plurality of circumferentially positioned stators which each include a stator core and a stator coil wound around the stator core, each of the plurality of magnetic members being positioned in circumferential alignment with a respective one of the stator cores of the stators; and
wherein each of the magnetic members of the housing directly contacts the respective stator core.

7. A blood pump apparatus comprising:
a housing including a blood inlet port through which blood enters the housing and a blood outlet port through which blood exits the housing;
the housing possessing a hollow interior defining a blood chamber in fluid communication with the blood inlet and the blood outlet;
an impeller rotatably positioned in the blood chamber to feed blood;
a plurality of magnetic material members mounted on the impeller so that the impeller and the plurality of magnetic material members rotate together as a unit within the blood chamber in the housing;
a motor stator positioned adjacent the housing for generating a magnetically attractive force to rotate the impeller;
a plurality of spaced apart magnetic members each positioned in a respective recess in the housing situated between the impeller and the motor stator so that the magnetic members directly transmit the magnetically attractive force generated by the motor stator to the magnetic material members of the impeller; and
a non-contact bearing mechanism for rotating the impeller without the impeller contacting the inner surface of the housing when the impeller is rotated by the motor stator.

8. The blood pump apparatus according to claim 7, wherein the motor stator includes a plurality of circumferentially arranged and spaced apart stators which each include a stator core and a stator coil wound around the stator core, each of the plurality of magnetic members being positioned in circumferential alignment with a respective one of the stator cores of the stators.

9. The blood pump apparatus according to claim 7, wherein the motor stator is mounted in a third housing member that is attachable to and detachable from the housing.

10. The blood pump apparatus comprising:
a housing including a blood inlet port through which blood enters the housing and a blood outlet port through which blood exits the housing;
the housing possessing a hollow interior defining a blood chamber in fluid communication with the blood inlet and the blood outlet;
an impeller rotatably positioned in the blood chamber to feed blood;
a plurality of magnetic material members mounted on the impeller so that the impeller and the plurality of magnetic material members rotate together as a unit within the blood chamber in the housing;
a motor stator positioned adjacent the housing for generating a magnetically attractive force to rotate the impeller;
a plurality of spaced apart magnetic members each positioned in a respective recess in the housing situated between the impeller and the motor stator so that the magnetic members transmit the magnetically attractive force generated by the motor stator to the magnetic material members of the impeller;
a non-contact bearing mechanism for rotating the impeller without the impeller contacting the inner surface of the housing when the impeller is rotated by the motor stator;
wherein the motor stator includes a plurality of circumferentially arranged and spaced apart stators which each include a stator core and a stator coil wound around the stator core, each of the plurality of magnetic members being positioned in circumferential alignment with a respective one of the stator cores of the stators; and
wherein each of the magnetic members of the housing directly contacts the respective stator core.

11. A blood pump apparatus comprising:
a housing having a blood inlet port and a blood outlet port;
a pump unit including an impeller rotatably mounted within the housing and provided with a plurality of magnetic material bodies, the impeller being rotatable within the housing to feed blood, and the magnetic material members rotating together with the impeller;
an impeller rotational torque generation section for generating a magnetically attractive force to rotate the impeller;
a plurality of magnetic members embedded in the housing between the impeller and the impeller rotational torque generation section for directly transmitting the magnetically attractive force generated by the impeller rotational torque generation section to the magnetic material members of the impeller; and
a non-contact bearing mechanism for rotating the impeller without the impeller contacting an inner surface of the housing when the impeller is rotated by the impeller rotational torque generation section.

12. The blood pump apparatus according to claim 11, wherein the impeller rotational torque generation section comprises a motor stator including a plurality of stators disposed on the circumference of a circle, the stators each include a stator core and a stator coil wound around the stator core, and each of the plurality of magnetic members is positioned in aligned relation with a respective one of the stator cores of the stators.

13. The blood pump apparatus according to claim 11, wherein the magnetic members of the housing and the stator cores directly contact each other.

14. The blood pump apparatus according to claim 11, wherein the impeller rotational torque generation section is attachable to and detachable from the pump unit.

15. The blood pump apparatus according to claim 11, wherein the magnetic member is a soft magnetic material.

16. The blood pump apparatus according to claim 11, further comprising a groove for a hydrodynamic bearing provided in an inner surface of the housing on a side of the housing opposite the impeller rotational torque generation section or in a surface of the impeller on a side facing away from the impeller rotational torque generation section.

17. The blood pump apparatus according to claim 11, further comprising second magnetic material on the impeller, and a permanent magnet or electromagnet mounted in the housing on a side opposite the impeller rotational torque generation section for attracting the second magnetic material of the impeller.

18. The blood pump apparatus according to claim 11, wherein the non-contact bearing mechanism is comprised of a groove for hydrodynamic bearing provided in an inner surface of the housing on an impeller rotational torque generation section side or in a surface of the impeller on the impeller rotational torque generation section side.

19. The blood pump apparatus according to claim 11, wherein the non-contact bearing mechanism is comprised of a second magnetic material provided in the impeller, an electromagnet provided in the housing on an opposite side to the impeller rotational torque generation section side and which attracts the second magnetic material of the impeller, and a position sensor for detecting the position of the impeller.

20. The blood pump apparatus according to claim 11, wherein the housing is made of synthetic resin or metal.

21. A blood pump apparatus comprising:
a housing comprising a blood inlet port through which blood enters and a blood outlet port through which blood exits, and a first housing member and a second housing member configured so that a blood chamber is formed between the first and second housing members, the blood chamber fluidly communicating with the blood inlet port and the blood outlet port;
an impeller rotatably positioned in the blood chamber to feed blood, and a plurality of first magnetic material members integrated with the impeller so that the impeller and the plurality of magnetic material members rotate together as a unit within the blood chamber in the housing, the impeller possessing oppositely facing surfaces each of which faces a respective inner surface of the housing;
a motor stator positioned adjacent the housing to generate a magnetically attractive force to rotate the impeller; and
a plurality of spaced apart magnetic members each positioned in a respective recess in the second housing member so that the magnetic members are located between the impeller and the motor stator for transmitting the magnetically attractive force generated by the motor stator to the magnetic material members of the impeller.

22. The blood pump apparatus according to claim 21, further comprising a non-contact bearing mechanism for rotating the impeller without the impeller contacting the inner surface of the housing when the impeller is rotated by the motor stator, the non-contact bearing mechanism comprising at least one of; i) a plurality of spaced apart grooves provided on at least one of said oppositely facing surfaces of the impeller or at least one of said inner surfaces of the housing; and ii) a second magnetic material member in the impeller, an electromagnet in the first housing member to attract the second magnetic material member, and a position sensor mounted in the first housing member to detect a position of the impeller.

23. The blood pump apparatus according to claim 22, wherein the non-contact bearing mechanism includes the plurality of grooves, and said plurality of grooves are provided on both of said inner surfaces of the housing.

24. The blood pump apparatus according to claim 22, wherein the non-contact bearing mechanism is comprised of a groove for hydrodynamic bearing provided in an inner surface of the housing on an impeller rotational torque generation section side or in a surface of the impeller on the impeller rotational torque generation section side.

25. The blood pump apparatus according to claim 22, wherein the non-contact bearing mechanism is comprised of a second magnetic material provided in the impeller, an electromagnet provided in the housing on an opposite side to a impeller rotational torque generation section side and which attracts the second magnetic material of the impeller, and a position sensor for detecting the position of the impeller.

26. The blood pump apparatus according to claim 21, wherein the housing is made of synthetic resin or metal.

* * * * *